United States Patent
Yoo et al.

(10) Patent No.: US 12,053,506 B2
(45) Date of Patent: *Aug. 6, 2024

(54) ROMO1-DERIVED ANTIMICROBIAL PEPTIDES AND VARIANTS THEREOF

(71) Applicant: KOREA UNIVERSITY RESEARCH AND BUSINESS FOUNDATION, Seoul (KR)

(72) Inventors: Young Do Yoo, Seoul (KR); Hye Ra Lee, Gyeonggi-do (KR)

(73) Assignee: KOREA UNIVERSITY RESEARCH AND BUSINESS FOUNDATION, Seoul (KR)

( * ) Notice: Subject to any disclaimer, the term of this patent is extended or adjusted under 35 U.S.C. 154(b) by 231 days.

This patent is subject to a terminal disclaimer.

(21) Appl. No.: 17/619,913

(22) PCT Filed: Jun. 17, 2020

(86) PCT No.: PCT/KR2020/007802
§ 371 (c)(1),
(2) Date: Dec. 16, 2021

(87) PCT Pub. No.: WO2020/256387
PCT Pub. Date: Dec. 24, 2020

(65) Prior Publication Data
US 2022/0362331 A1    Nov. 17, 2022

(30) Foreign Application Priority Data

Jun. 17, 2019  (KR) ........................ 10-2019-0071635

(51) Int. Cl.
A61K 38/17    (2006.01)
A61P 31/00    (2006.01)
A61P 31/04    (2006.01)

(52) U.S. Cl.
CPC .......... *A61K 38/1709* (2013.01); *A61P 31/00* (2018.01); *A61P 31/04* (2018.01)

(58) Field of Classification Search
None
See application file for complete search history.

(56) References Cited

U.S. PATENT DOCUMENTS

| | | | |
|---|---|---|---|
| 5,459,237 A | 10/1995 | Berkowitz et al. | |
| 2005/0272067 A1 | 12/2005 | Macina et al. | |
| 2011/0201048 A1 | 8/2011 | Yoo et al. | |

FOREIGN PATENT DOCUMENTS

| | | |
|---|---|---|
| CN | 1699409 A | 11/2005 |
| CN | 1699416 A | 11/2005 |
| CN | 109415412 A | 3/2019 |
| EP | 1693381 A1 | 8/2006 |
| KR | 10-2011-0083301 A | 5/2012 |
| KR | 101875057 B1 | 7/2018 |
| KR | 101983679 B1 | 5/2019 |
| WO | 2005015206 A2 | 2/2005 |
| WO | WO-2005015206 A2 * | 2/2005 ................ A61P 1/00 |
| WO | WO-2017221274 A2 * | 12/2017 ............. A01N 37/46 |

OTHER PUBLICATIONS

Chung et al. ("A novel protein, Romo1, induces ROS production in the mitochondria," Biochemical and Biophysical Research Communications 347 (2006) 649-655) (Year: 2006).*
Sha et al. ("Antibacterial potential of hGlyrichin encoded by a human gene," J. Pept. Sci. 2012; 18: 97-104) (Year: 2012).*
International Search Report from related International Application No. PCT/KR2020/007802, dated Sep. 18, 2020, 6 pages.
Written Opinion from related International Application No. PCT/KR2020/007802, dated Sep. 18, 2020, 5 pages.
WHO, Global Priority List of Antibiotic-Resistant Bacteria to Guide Research, Discovery, and Development of New Antibiotics, Feb. 27, 2017, 7 pages.
Lee et al., J. Cell Biol., 217, 2059-2071, 2018.
Lee, G. Y. et al., Romo1 is a mitochondrial nonselective cation channel with viroporin-like characteristics/.
NCBI, NCBI Reference Sequence No. NP_001090931.2, reactive oxygen species modulator 1 [Sus scrofa], Nov. 11, 2018, 2 pages.
Lee, Hye-Ra, et al., Romo1-Derived Antimicrobial Peptide Is a New Antimicrobial Agent against Multidrug-Resistant Bacteria in a Murine Model of Sepsis, American Society for Microbiology, Molecular Biology and Physiology, vol. 11, Issue 2, e03258-19, Mar./Apr. 2020, 13 pages.
Kim et al; "Antibacterial and Antibiofilm Activity and Mode of Action of Magainin 2 against Drug-Resistant Acinetobacter baumannii"; Int. J. Mol. Sci. 2018, 19, 3041; 14 pages; doi:10.3390 /ijms 19103041.
Non-Final Office Action issued in U.S. Appl. No. 17/619,918, mailed on Oct. 11, 2023.
Partial Supplementary European Search Report issued in European Patent Application No. 20827933.1, mailed on Dec. 21, 2023.
Database GenPept (Online); NCBI; "Predicted: reactive oxygen species modulator 1, partial [Nestor notabilis]"; Oct. 31, 2014.

* cited by examiner

*Primary Examiner* — Christina Bradley
(74) *Attorney, Agent, or Firm* — Dilworth IP, LLC

(57) ABSTRACT

The present invention relates to antimicrobial peptides derived from Romo1 protein, and specifically, provides various peptides having the amino acid sequence of the α-helix 2 region of the Romo1 protein and an antibacterial composition containing each of the peptides, as a result of confirming that the peptides have antibacterial activity against gram-positive, gram-negative and multidrug-resistant bacteria. The Romo1-derived peptides and variants thereof have better bactericidal capability against various types of bacteria and multidrug-resistant bacteria than existing antibiotics and antibiotic peptides, and have antibacterial activity against various bacteria in blood vessels, and may be provided as substances for the prevention or treatment of a wide range of bacterial infectious diseases. Thus, a composition containing the antimicrobial peptide of the present invention is expected to be used in various applications, including drugs, quasi-drugs, food and feed additives, pesticide and cosmetic additives, to prevent or treat infectious diseases.

4 Claims, 5 Drawing Sheets

Specification includes a Sequence Listing.

ROMO1-DERIVED ANTIMICROBIAL PEPTIDES AND VARIANTS THEREOF

REFERENCE TO AN ELECTRONIC SEQUENCE LISTING

The contents of the electronic sequence listing (393-024US_BPX200020_SequenceListing.txt; Size: 16,819 bytes; and Date of Creation: Jun. 15, 2020) is herein incorporated by reference in its entirety.

TECHNICAL FIELD

The present invention relates to antimicrobial peptides derived from Romo1 protein, and specifically, provides various peptides having the amino acid sequence of the α-helix 2 region of the Romo1 protein and an antibacterial composition containing each of the peptides, as a result of confirming that the peptides have antibacterial activity against gram-positive, gram-negative and multidrug-resistant bacteria.

BACKGROUND ART

The biggest problem with antibiotics that are used as therapeutic means against bacterial infections is that bacteria acquire antibiotic resistance. According to the UK government's Welcome Trust report, it is predicted that, in 2050, the number of deaths worldwide due to superbacteria that cannot be treated with existing antibiotics will exceed 10,000,000, and thus superbacterial infection will overtake cancer as a cause of death.

In addition, the World Health Organization (WHO) selected carbapenem-resistant *Acinetobacter baumannii*, carbapenem-resistant *Pseudomonas aeruginosa*, carbapenem-resistant Enterobacteriaceae sp. strains as bacteria in the critical priority category among many multidrug-resistant bacteria, and announced that the top priority should be given to resolving gram-negative superbacteria that are resistant to carbapenem-based antibiotics known as the last antibiotics.

Meanwhile, bacteremia refers to a condition in which bacteria are alive in the blood, and sepsis is caused by the direct or indirect effect of infection. That is, sepsis is a systemic inflammatory reaction syndrome caused by the infection of blood with bacteria invading the human body, and is a disease having a survival rate of less than 30% 6 hours after infection. Bacteria causing sepsis are very diverse, including streptococci, *Staphylococcus aureus*, *Escherichia coli*, pneumococcus, *Pseudomonas aeruginosa*, and fungi, and the treatment of sepsis is difficult due to the diversity of these bacteria causing sepsis.

To date, the best treatment for sepsis is mainly for the purpose of alleviating symptoms, such as suppressing immune response or inhibiting blood coagulation. For the fundamental treatment of sepsis, bacterial identification for identifying the bacterial species infecting the patient is required at the initial stage. However, there is a problem in that the time required for bacterial identification is not secured due to the immediate systemic inflammatory reaction caused by sepsis as described above. In addition, even if a sepsis-causing bacterium has been successfully identified, when the sepsis-causing bacterium is a multidrug-resistant bacterium that is resistant to antibiotics, a problem arises in that there is no drug suitable for treatment thereof. Accordingly, it is necessary to develop antibiotics having antibacterial activity against a wide range of bacteria without identification of sepsis-causing bacteria, and in particular, it is required to develop antibiotics having antibacterial activity against multidrug-resistant bacteria.

As described above, the biggest problem with antibiotics used by mankind to date is that bacteria acquire resistance. To solve this problem, many studies have been conducted, and in particular, the development of antimicrobial peptides (AMPs) has been actively made to overcome antibiotic resistance acquired by bacteria. Various antimicrobial peptides derived from animal or human host defense proteins have been developed, but have problems in that there is a possibility of acquiring resistance by bacteria in the human immune system, and in that they have short half-life in blood, are toxic to the human body, and show limited medicinal effects compared to existing antibiotics. Due to these problems, the antimicrobial peptides have not been put to practical use. For example, magainin is an antimicrobial peptide developed in the United States in 1999, and FDA approval thereof was requested after phase 3 clinical trials, but the approval was rejected because the medicinal effect thereof was not better than those of conventional antibiotics. In addition, daptomycin in 2003 and oritavancin in 2014 were approved by the US Food and Drug Administration, but the two peptides all showed antibacterial activity only against gram-positive bacteria, and could be applied only to skin infectious diseases.

As described above, due to limited medicinal effects and applications, antimicrobial peptides applicable to the treatment of bacterial infectious diseases such as bacteremia and sepsis have not yet been developed. The present inventors have found that the α-helix 2 structure of the Romo1 protein located in the inner mitochondrial membrane exhibits antibacterial activity against gram-positive, gram-negative and multidrug-resistant bacteria, and thus may be applied for the treatment of a wide range of bacterial infectious diseases, thereby completing the present invention.

PRIOR ART DOCUMENTS (Non-Patent Document 1): WHO, Global Priority List of Antibiotic-Resistant Bacteria to Guide Research, Discovery, and Development of New Antibiotics (2017 Feb. 27)

(Non-Patent Document 2): Lee et al., J. Cell Biol., 217, 2059-2071, 2018

DISCLOSURE

Technical Problem

An object of the present invention is to provide an antimicrobial peptide derived from Romo1 protein and a modified antimicrobial peptide resulting from substitution or deletion of some amino acids of the peptide.

Another object of the present invention is to provide an antibiotic containing the antimicrobial peptide as an active ingredient, and a food and feed additive, a cosmetic composition, a biopesticide, and an antibacterial quasi-drug composition, which each contain the antimicrobial peptide.

However, the objects to be achieved by the present invention are not limited to the above-mentioned objects, and other objects not mentioned herein will be clearly understood by those skilled in the art from the following description.

Technical Solution

One aspect provides an antimicrobial peptide comprising a sequence of 7 to 28 contiguous amino acids extending in the carboxy (C)-terminal direction starting at any amino acid selected from the 52-79 amino acid region of the Romo1 protein sequence consisting of the amino acid sequence set forth in SEQ ID NO: 1.

One embodiment provides an antimicrobial peptide resulting from substitution or deletion of at least one amino acid of the amino acid sequence constituting the antimicrobial peptide.

In another embodiment, the peptide may be a peptide comprising or consisting of any one amino acid sequence selected from the group consisting of SEQ ID NOS: 2 to 15.

In another embodiment, the peptide may be a peptide comprising or consisting of any one amino acid sequence selected from the group consisting of SEQ ID NOS: 16, 30, 40 and 45.

In another embodiment, the peptide consisting of the amino acid sequence of SEQ ID NO: 16 may consist of, for example, any one amino acid sequence selected from the group consisting of SEQ ID NOs: 17 to 29.

In another embodiment, the peptide consisting of the amino acid sequence of SEQ ID NO: 30 may consist of, for example, any one amino acid sequence selected from the group consisting of SEQ ID NOs: 31 to 39.

In another embodiment, the peptide consisting of the amino acid sequence of SEQ ID NO: 40 may consist of, for example, any one amino acid sequence selected from the group consisting of SEQ ID NOs: 41 to 44.

In another embodiment, the peptide consisting of the amino acid sequence of SEQ ID NO: 45 may consist of, for example, any one amino acid sequence selected from the group consisting of SEQ ID NOs: 46 and 47.

In another embodiment, the peptide may be preferably a peptide comprising or consisting of any one amino acid sequence selected from the group consisting of SEQ ID NOS: 17 to 25, 27, 34, 37, 39, 42 and 44, more preferably a peptide comprising or consisting of any one amino acid sequence selected from the group consisting of SEQ ID NOS: 22, 23 and 24.

In another embodiment, the peptide may be an antimicrobial peptide consisting of either the amino acid sequence of SEQ ID NO: 13, or a sequence comprising at least one amino acid substitution selected from among the following (a) to (h) with respect to the amino acid sequence of SEQ ID NO: 13. (a) a K to R substitution at amino acid position 1, (b) a T to K or R substitution at amino acid position 2, (c) a Q to K or R substitution at amino acid position 5, (d) an S to K, R or H substitution at amino acid position 6, (e) a T to K or R substitution at amino acid position 9, (f) an F to W substitution at amino acid position 10, (g) an I to L substitution at amino acid position 16, and (h) an I to G or L substitution at amino acid position 20.

In another embodiment, the antimicrobial peptide may be one in which at least one methionine is substituted with norleucine or isoleucine.

In another embodiment, the antimicrobial peptide may be one in which any one of amino acids at positions 3, 4, 5, 7, 8, 9, 11, 17, 18 and 19 is deleted, or an amino acid at position 3 or 4 and an amino acid at position 7 or 8 are deleted.

In another embodiment, the antimicrobial peptide may further comprise an amino acid sequence linked to the C-terminus, and the amino acid sequence linked to the C-terminus may consist of a sequence of one to three repeating R or K.

In another embodiment, the peptide may be one in which at least one amino acid in the sequence thereof is modified.

In another embodiment, the modification may be PEGylation, acetylation, carboxylation, lipidation, or amidation.

In another embodiment, the amino acids constituting the peptide may be each independently L- or D-amino acids, and may be radioactively or fluorescently labeled amino acid analogues.

In another embodiment, the peptide may have antibacterial activity against one or more bacteria selected from the group consisting of gram-positive bacteria, gram-negative bacteria, and multidrug-resistant bacteria.

In another embodiment, the gram-positive bacteria may be bacteria belonging to one genus selected from the group consisting of *Staphylococcus* sp., *Bacillus* sp., *Enterococcus* sp., *Streptomyces* sp., and *Streptococcus* sp. Preferably, the gram-positive bacteria may be one or more bacteria selected from the group consisting of *Staphylococcus aureus, Bacillus subtilis, Enterococcus faecium, Streptomyces sindenensis, Enterococcus faecalis*, and *Streptococcus pneumoniae*.

In another embodiment, the gram-negative bacteria may be bacteria belonging to one genus selected from the group consisting of *Escherichia* sp., *Klebsiella* sp., *Acinetobacter* sp., *Pseudomonas* sp., and *Enterobacter* sp. Preferably, the gram-negative bacteria may be one or more bacteria selected from the group consisting of *Escherichia coli, Klebsiella pneumoniae, Acinetobacter baumannii, Pseudomonas aeruginosa*, and *Enterobacter aerogenes*.

In another embodiment, the multidrug-resistant bacteria may be the above-described gram-positive or gram-negative bacteria having resistance to one or more antibiotics belonging to penicillins, carbapenems, cephalosporins, quinolones, macrolides, tetracyclins, or glycopeptides. Preferably, the multidrug-resistant bacteria may be bacteria belonging to one genus selected from the group consisting of methicillin-resistant *Staphylococcus* sp., multidrug-resistant *Pseudomonas* sp., vancomycin-resistant *Enterococcus* sp., multidrug-resistant *Klebsiella* sp; multidrug-resistant *Acinetobacter* sp., and vancomycin-resistant *Staphylococcus* sp.

In another embodiment, the multidrug-resistant bacteria may be one or more bacteria selected from the group consisting of methicillin-resistant *S. aureus*, multidrug-resistant *P. aeruginosa*, multidrug-resistant *A. baumannii*, multidrug-resistant *K. pneumoniae*, vancomycin-resistant *E. faecium*, and vancomycin-resistant *S. aureus*.

In another embodiment, the multidrug-resistant *P. aeruginosa* may have resistance to one or more antibiotics selected from the consisting group of piperacillin, piperacillin-tazobactam, ceftazidime, imipenem, meropenem, gentamicin, amikacin, and ciprofloxacin; the multidrug-resistant *A. baumannii* may have resistance to one or more antibiotics selected from the group consisting of piperacillin, piperacillin-tazobactam, ceftazidime, imipenem, meropenem, gentamicin, amikacin, ciprofloxacin, and cefepime; and the multidrug-resistant *K. pneumoniae* may have resistance to one or more antibiotics selected from the group consisting of piperacillin-tazobactam, ceftazidime, cefepime, imipenem, gentamicin, and ciprofloxacin.

In another embodiment, the vancomycin-resistant *E. faecium* may have, in addition to resistance to vancomycin, resistance to one or more antibiotics selected from the group consisting of rifampin, tetracycline, gentamicin, erythromycin, streptomycin, and ampicillin, and the vancomycin-resistant *S. aureus* may have, in addition to resistance to vancomycin, resistance to one or more antibiotics selected from the group consisting of oxacillin, benzylpenicillin, ampicillin, and cefazolin.

Another aspect provides an antibiotic containing the antimicrobial peptide as an active ingredient.

Still another aspect provides a pharmaceutical composition for preventing or treating bacterial infectious disease containing the antimicrobial peptide as an active ingredient.

Yet another aspect provides a method for preventing or treating bacterial infectious disease comprising a step of administering the antimicrobial peptide to a subject.

Still yet another aspect provides the use of the antimicrobial peptide for the manufacture of a medicament for preventing or treating bacterial infectious disease.

In one embodiment, the bacterial infectious disease may be one or more diseases selected from the group consisting of skin infection, food poisoning, otitis media, cystitis, peritonitis, urinary tract infection, mastitis, pneumonia, endocarditis, conjunctivitis, arthritis, endometritis, strangles, bacteremia, sepsis, and acne, and may preferably be pneumonia or sepsis.

A further aspect provides an antibacterial quasi-drug composition, a cosmetic composition, a food additive, and a feed additive, which each contain the antimicrobial peptide.

Advantageous Effects

The Romo1-derived peptide and variants thereof according to the present invention may have higher antibacterial activity against various types of bacteria than existing antibiotics and antibiotic peptides, and thus may simultaneously remove various causative bacteria from the blood of patients with bacterial infectious diseases at an early stage. In particular, the peptide of the present invention may exhibit high antibacterial activity against antibiotic-resistant bacteria, and thus may be provided as a preventive or therapeutic agent for infectious diseases, caused by multidrug-resistant bacteria, beyond the limits of application of existing antibiotics. In addition, the Romo1-derived peptide and variants thereof according to the present invention are expected to be used for the purpose of preventing or treating a wide range of bacterial infectious diseases in various applications, including medicines, quasi-drugs, food and feed additives, pesticides and cosmetic additives, in that they have a low probability of acquiring resistance thereto by bacteria, have low toxicity, and particularly have higher antibacterial activity than existing antimicrobial peptides in the blood.

MODE FOR INVENTION

Figure 1:
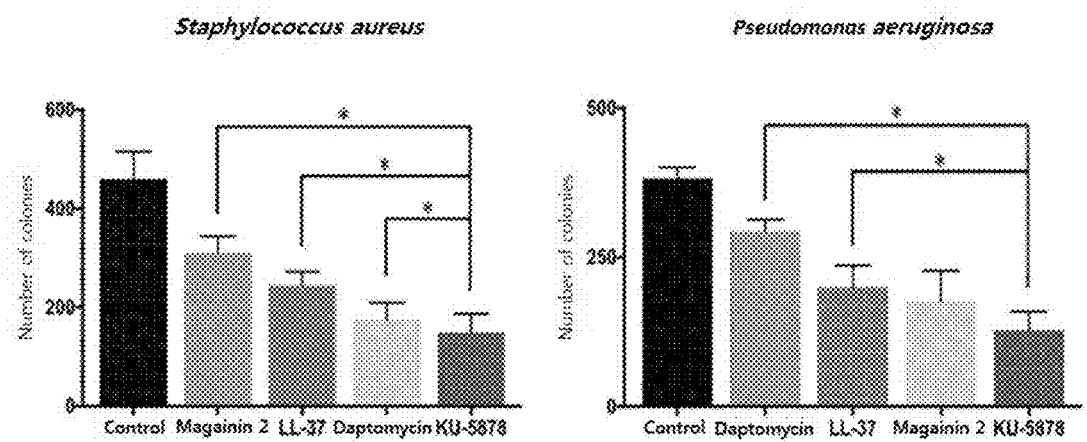
FIG. 1 shows the results of comparing the antibacterial activity of KU-5878 with those of conventional antimicrobial peptides (LL-37, magainin 2, and daptomycin) against gram-positive and gram-negative bacteria.

Reactive oxygen species modulator 1 (Romo1) protein is a membrane protein located in the inner membrane of mitochondria, and is known to be involved in mitochondrial reactive oxygen production, TNF-α signaling, cell aging, cancer progression and invasion, and mitochondrial protein transport, etc. The structure of the Romo1 protein is a protein comprising two alpha helices, wherein the α-helix 1 is mainly composed of hydrophobic amino acids, and the α-helix 2 has both hydrophilicity and hydrophobicity.

The present inventors excluded the α-helix 1 region of the Romo1 protein from the study because this region does not dissolve well in water. The present inventors have synthesized peptides of various lengths having the amino acid sequence (52 to 79 a.a.) of the α-helix 2 region, evaluated the antibacterial activities thereof, and found that variants of the peptides have antibacterial activity, thereby completing the present invention.

In a specific embodiment of the present invention, the present inventors synthesized several peptides of different lengths comprising a sequence of contiguous amino acids starting at one amino acid selected from the 52-79 amino acid region of the Romo1 protein, and the inventors evaluated the antibacterial activity of each of the peptides against *Pseudomonas aeruginosa* and *Staphylococcus aureus* using minimum bactericidal concentration assay. As a result, it was confirmed that all the peptides comprising a sequence of 18 contiguous amino acids starting at any amino acid selected from the 52-62 amino acid region of the Romo1 protein had antibacterial activity against *P. aeruginosa* and *Staphylococcus aureus*. Particularly, it could be confirmed that a KU-5878 peptide comprising the 58-78 amino acid sequence of the Romo1 protein had excellent antibacterial activity (see Example 1).

Accordingly, the present invention provides a Romo1-derived antimicrobial peptide.

In the present specification, the "Romo1-derived peptide" is a peptide comprising a sequence of contiguous amino acids from the 52-79 amino acid region of the Romo1 protein consisting of the amino acid sequence set forth in SEQ ID NO: 1, and the "peptide" refers to a linear molecule formed of amino acid residues liked together by peptide bonds. The Romo1-derived peptide may be obtained by fragmenting the Romo1 protein, and it may be produced according to a chemical synthesis method known in the art, particularly, a solid-phase synthesis technique or a liquid-phase synthesis technique.

Furthermore, the length of the Romo1-derived peptide of the present invention is not limited as long as the peptide comprises a sequence of contiguous amino acids starting at any amino acid selected from the 52 to 79 amino acid region of the Romo1 protein sequence consisting of the amino acid sequence set forth in SEQ ID NO: 1, but the length may be preferably 7 to 28 mer, more preferably 18 to 28 mer.

More specifically, the antimicrobial peptide may comprise a sequence of 18 contiguous amino acids starting at any amino acid selected from the 52-62 amino acid region of the Romo1 protein sequence. Preferably, the antimicrobial peptide may comprise any one amino acid sequence selected from the group consisting of SEQ ID NOS: 2 to 15, more preferably from the group consisting of SEQ ID NOs: 5, 8, 9, 13 and 14.

In the present specification, the amino acids are listed in order from the N-terminus to the C-terminus, and the expression "sequence of contiguous amino acids" starting at an amino acid selected from a specific region of the Romo1 protein sequence refers to a sequence of contiguous amino acids extending in the C-terminal direction starting at the selected amino acid. In addition, in the present specification, the expression "sequence of 7 to 28 contiguous amino acids" starting at any amino acid selected from a specific region of the Romo1 protein refers to a sequence consisting of a total of 7 to 28 contiguous amino acids, including the starting amino acid selected from a specific region of the Romo1 protein and including contiguous amino acids extending in the C-terminal direction starting at the starting amino acid.

In a specific embodiment of the present invention, the present inventors selected a KU-5878 peptide comprising the amino acid sequence set forth in SEQ ID NO: 13 as a representative to confirm the range of application of the Romo1-derived antimicrobial peptide, and evaluated the antibacterial activity of the peptide against *Staphylococcus aureus, Bacillus subtilis, Enterococcus faecium, Streptomyces sindenensis, Enterococcus faecalis, Streptococcus pneumoniae, Escherichia coli, Klebsiella pneumoniae, Acinetobacter baumannii, Pseudomonas aeruginosa, Enterobacter aerogenes*, methicillin-resistant *S. aureus*, multidrug-resistant *P. aeruginosa*, multidrug-resistant *A. baumannii*, multidrug-resistant *K. pneumoniae*, vancomycin-resistant *E. faecium*, and vancomycin-resistant *S. aureus*. As a result, it could be seen that the Romo1-derived antimicrobial peptide of the present invention exhibited a wide spectrum of antibacterial activity against all gram-positive bacteria, gram-negative bacteria and multidrug-resistant bacteria (see Example 2).

In addition, in order to identify peptides having better antibacterial activity, the amino acids constituting KU-5878 were classified into $X_1X_1MMX_1X_1GGX_1FGXIFMAIGMGIR$ (SEQ ID NO: 16), $KTX_2X_2QSGGTFGTFX_2AX_2GX_2GX_2R$ (SEQ ID NO: 30), $KTMMQSGGTX_3GTX_3MAIGMGIR$ (SEQ ID NO: 40), and $KTMMQSX_4X_4TFX_4TFMX_4IX_4MX_4IR$ (SEQ ID NO: 45) depending on the properties thereof, peptides in which each of the amino acids $X_1$ to $X_4$ has been substituted were synthesized, and the antibacterial activities thereof were evaluated.

In a specific example of the present invention, the present inventors examined changes in the antibacterial activity of the KU-5878 peptide when hydrophilic amino acid residues in the KU-5878 peptide were substituted with positively charged amino acids. In the KU-5878 peptide, the positions of the hydrophilic amino acid residues are marked with $X_1$ in SEQ ID NO: 16, and the amino acids at positions $X_1$ were each independently substituted. It was confirmed that, when the hydrophilic amino acid in the α-helix 2 region of the Romo1 protein was substituted with a positively charged amino acid (R, H or K) or another hydrophilic amino acid (T, S, Q or N), the antibacterial activity thereof changed. As a result, it could be seen that the antibacterial activity of the peptide was maintained or better antibacterial activity was exhibited (see Example 4-1).

In another specific example of the present invention, the present inventors examined changes in the antibacterial activity of the KU-5878 peptide when methionine (M) or isoleucine (I) in the KU-5878 peptide was substituted with a hydrophobic amino acid residue (M, L, I, V or Nle) having a structure similar thereto and when methionine (M) or isoleucine (I) in the KU-5878 peptide was substituted with a hydrophobic amino acid residue (F, Y, or W) having a structure different therefrom. In the KU-5878 peptide, methionine (M) and isoleucine (I) are marked with $X_2$ in SEQ ID NO: 30, and the amino acids at positions $X_2$ were each independently substituted. As a result, when methionine was substituted with norleucine (Nle), the antibacterial activity of the peptide was maintained, and when isoleucine was substituted with tryptophan (W), the antibacterial activity of the peptide decreased. On the other hand, it was confirmed that, when isoleucine was substituted with glycine, a peptide with improved antibacterial activity could be obtained (see Example 4-3).

In another specific example of the present invention, the present inventors examined changes in the antibacterial activity of the KU-5878 peptide when the hydrophobic residue phenylalanine (F) in the KU-5878 peptide was substituted with a hydrophilic amino acid or a hydrophobic amino acid (F, Y or W) having a structure similar thereto (F, Y, or W) or a hydrophobic amino acid (M, L, I, V or Nle) having a structure different therefrom. In the KU-5878 peptide, phenylalanine is marked with $X_3$ in SEQ ID NO: 40, and the amino acids at positions $X_3$ were each independently substituted. As a result, it was confirmed that, when phenylalanine was substituted with tryptophan (W), a peptide with improved antibacterial activity could be obtained (see Example 4-4).

In another specific example of the present invention, the present inventors examined changes in the antibacterial activity of KU-5878 when alanine (A) or glycine (G) in KU-5878 was substituted with glycine or alanine. In the KU-5878 peptide, alanine and glycine are marked with $X_4$ in SEQ ID NO: 45, and the amino acids at positions $X_4$ were each independently substituted. As a result, it was confirmed that, when alanine was substituted with glycine and when glycine was substituted with alanine, the peptide exhibited antibacterial activity, but exhibited decreased antibacterial activity compared to the KU-5878 peptide (see Example 4-5).

From the foregoing, the Romo1-derived peptide of the present invention comprises a sequence of 7 to 28 contiguous amino acids starting at any amino acid selected from the 52-79 amino acid region of Romo1, and at the same time, may comprise at least one amino acid substitution within a range in which it exhibits antibacterial activity.

In a specific example of the present invention, the present inventors selected KU-5878-K4 as a representative in order to confirm the scope of application of the KU-5878 variants, and the inventors evaluated the antibacterial activity of KU-5878-K4 against various bacteria. As a result, it could be seen that, like KU-5878, KU-5878-K4 also exhibited a wide spectrum of antibacterial activity against all the gram-positive bacteria, gram-negative bacteria and multidrug-resistant bacteria (see Example 4-2).

In addition, through specific examples, the present inventors could see that even a peptide obtained by substituting some or all of the amino acids constituting each of KU-5878 and KU-5878-K4 with D-amino acids exhibited antibacterial activity similar to that of KU-5878, and especially in the presence of bovine serum, KU-5878 and KU-5878-K4 exhibited significantly decreased antibacterial activity, but the decrease in antibacterial activity of the variant obtained by substitution with D-amino acids was small (see Example 4-6).

From the foregoing, the amino acids constituting the Romo1-derived peptide of the present invention may be each independently L- or D-amino acids, and each of the amino acids may be an amino acid analog, a radioactively labeled amino acid, or a fluorescently tagged amino acid.

Meanwhile, a portion of the amino acid sequence of the Romo1-derived peptide of the present invention may be selected and modified at the amino (N-) terminus or the carboxy (C-) terminus in order to increase the activity thereof. Through this modification, the peptide of the present invention may have an increased half-life when administered in vivo.

Through a specific example, the present inventors confirmed that a KU-5878 variant amidated at the C-terminus had increased antibacterial activity (see Example 5).

Thus, a protecting group such as an acetyl group, a fluorenyl methoxycarbonyl group, a formyl group, a palmitoyl group, a myristyl group, a stearyl group, or polyethylene glycol (PEG) may be bonded to the amino terminus of the Romo1-derived peptide of the present invention, and the carboxy terminus of the peptide may be modified with a hydroxyl group (—OH), an amino group (—NH$_2$), an azide group (—NHNH$_2$), or like. In the addition, fatty acids, oligosaccharide chains, any nanoparticles (gold particles, liposomes, heparin, hydrogel, etc.), amino acids, carrier proteins or the like may be bonded to the termini of the peptide of the present invention or the R-groups of the amino acids. The above-described amino acid modification acts to improve the potency and stability of the peptide of the present invention. In the present specification, the term "stability" refers not only to in vivo stability, but also to storage stability (including storage stability during room temperature storage, cold storage, or frozen storage).

Meanwhile, the Romo1-derived antimicrobial peptide of the present invention may be a peptide in which one or more of the amino acids constituting the same are deleted. According to the foregoing, it could be confirmed that a peptide obtained by substitution, modification, or deletion of one or more of the amino acids constituting the Romo1-derived peptide of the present invention also exhibited antibacterial activity. Thus, the present invention may provide a Romo1-derived peptide variant as an antimicrobial peptide.

In the present invention, the term "variant" refers to a peptide in which one or more of the amino acids constituting the Romo1-derived peptide are substituted, modified, and/or deleted within the range in which it exhibits antibacterial activity. As long as the variant exhibits antibacterial activity, it is considered a variant exhibiting better antibacterial activity than the Romo1-derived peptide of the present invention and is not particularly limited.

The antimicrobial peptide of the present invention may consist of either the amino acid sequence of SEQ ID NO: 13, or a sequence comprising at least one amino acid substitution selected from among the following (a) to (h) with respect to the amino acid sequence of SEQ ID NO: 13.

(a) a K to R substitution at amino acid position 1, (b) a T to K or R substitution at amino acid position 2, (c) a Q to K or R substitution at amino acid position 5, (d) an S to K, R or H substitution at amino acid position 6, (e) a T to K or R substitution at amino acid position 9, (f) an F to W substitution at amino acid position 10, (g) an I to L substitution at amino acid position 16, and (h) an I to G or L substitution at amino acid position 20. According to Examples 8 and 9, the present inventors confirmed that, when one or more amino acids in the amino acid sequence of KU-5878 were substituted with any one of (a) to (h) above, the antibacterial effect of the peptide was improved.

In another embodiment, the antimicrobial peptide may be one in which at least one methionine is substituted with norleucine or isoleucine. Norleucine has the same structure as methionine, except that sulfur (S) is substituted with carbon, and isoleucine is common to norleucine in that it has an alkyl substituent having the same number of carbon atoms as that of norleucine. The present inventors confirmed that, when any one or more of the 4 methionines in the amino acid sequence of KU-5878 were substituted with norleucine, the antibacterial activity of the peptide was improved (see Table 13).

In another embodiment, the antimicrobial peptide may be one in which any one of amino acids at positions 3, 4, 5, 7, 8, 9, 11, 17, 18 and 19 is deleted, or an amino acid at position 3 or 4 and an amino acid at position 7 or 8 are deleted. According to Examples 6 and 7 of the present application, when any one of the amino acids at positions 3, 4, 5, 7, 8, 9, 11, 17, 18 and 19 in KU-5878 was deleted, the antibacterial activity of the peptide increased, and the same effect may be expected for a peptide in which some amino acids of KU-5878 are substituted.

In another embodiment, the antimicrobial peptide may further comprise an amino acid sequence linked to the C-terminus thereof, wherein the amino acid sequence linked to the C-terminus may consist of a sequence of one to three repeating R or K. According to Example 10, the present inventors confirmed that, when an amino acid sequence consisting of RRR or KK was further added to the C-terminus of KU-5878, the antibacterial activity of the peptide increased.

The Romo1-derived peptide and variants thereof according to the present invention have antibacterial activity against gram-positive bacteria, gram-negative bacteria and multidrug-resistant bacteria. Thus, the present invention may provide a pharmaceutical composition for preventing or treating bacterial infectious disease containing the antimicrobial peptide as an active ingredient.

Non-limiting examples of the gram-positive bacteria whose proliferation and/or growth is inhibited by the Romo1-derived peptide and variants thereof according to the present invention include *Staphylococcus* sp., *Bacillus* sp., *Enterococcus* sp., *Streptomyces* sp., and *Streptococcus* sp. Preferably, the gram-positive bacteria may be *Staphylococcus aureus, Bacillus subtilis, Enterococcus faecium, Streptomyces sindenensis, Enterococcus faecalis*, and/or *Streptococcus pneumoniae*.

In addition, non-limiting examples of the gram-positive bacteria whose proliferation and/or growth is inhibited by the Romo1-derived peptide and variants thereof according to the present invention include *Escherichia* sp., *Klebsiella* sp., *Acinetobacter* sp., *Pseudomonas* sp., and *Enterobacter* sp. Preferably, the gram-positive bacteria may be *Escherichia coli, Klebsiella pneumoniae, Acinetobacter baumannii, Pseudomonas aeruginosa*, and/or *Enterobacter aerogenes*.

In addition, the Romo1-derived peptide and variants thereof according to the present invention have antibacterial activity against multidrug-resistant bacteria. Thus, the multidrug-resistant bacteria whose proliferation and/or growth is inhibited by the Romo1-derived peptide and variants thereof may be the above-described gram-positive bacteria or gram-negative bacteria having resistance to one or more antibiotics belonging to penicillins, carbapenems, cephalosporins, quinolones, macrolides, tetracyclins, or glycopeptides. Preferably, the multidrug-resistant bacteria may be methicillin-resistant *Staphylococcus* sp., multidrug-resistant *Pseudomonas* sp., vancomycin-resistant *Enterococcus* sp., multidrug-resistant *Klebsiella* sp., multidrug-resistant *Acinetobacter* sp., and/or vancomycin-resistant *Staphylococcus* sp.

The present invention may provide a pharmaceutical composition containing the Romo1-derived peptide and/or a variant thereof as an active ingredient, that is, an antibiotic. The "bacterial infectious disease" to be prevented or treated by the pharmaceutical composition of the present invention may be a disease caused by infection with the gram-positive bacteria, gram-negative bacteria and/or multidrug-resistant bacteria. Preferably, the bacterial infectious disease may be skin infection, food poisoning, otitis media, cystitis, peritonitis, urinary tract infection, mastitis, pneumonia, endocarditis, conjunctivitis, arthritis, endometritis, strangles, bacteremia, sepsis, and/or acne, which are/is caused by infection with the bacteria. More preferably, the bacterial infectious disease may be sepsis or pneumonia.

The present invention also provides a method for preventing or treating bacterial infectious disease comprising a step of administering the Romo1-derived peptide and/or a variant thereof to a subject.

In the present invention, the "subject" is not limited as long as it is a mammal. Preferably, the subject may be a human or livestock.

In the present invention, the term "preventing" means any action of delaying infection with the gram-positive bacteria, gram-negative bacteria and/or multidrug-resistant bacteria or delaying the onset of a disease caused by the infection, by administration of the pharmaceutical composition according to the present invention. The term "treating" means any action of alleviating or beneficially changing symptoms of bacterial infection by administration of the pharmaceutical composition according to the present invention.

In the present invention, the pharmaceutical composition may further contain one or more known antibiotics in addition to the Romo1-derived peptide and/or variants thereof, and may further contain suitable carriers, excipients and diluents that are commonly used in the preparation of pharmaceutical compositions.

In the present invention, the "carrier" is also called a vehicle, and refers to a compound that facilitates the incorporation of a protein or peptide into cells or tissues. For example, dimethyl sulfoxide (DMSO) is a commonly used carrier that facilitates the uptake of many organic compounds into the cells or tissues of an organism.

In the present invention, the "diluent" is defined as a compound diluted in water that will dissolve a target protein or peptide, as well as stabilize the biologically active form of the protein or peptide. Salts dissolved in buffer solutions are used as diluents in the art. A commonly used buffer solution is phosphate buffered saline because it mimics the salt conditions of human solutions. Since buffer salts can control the pH of a solution at low concentrations, a buffered diluent rarely modifies the biological activity of the compound. Compounds including azelaic acid as used herein may be administered to a human patient as it is, or as a pharmaceutical composition mixed with other ingredients or with a suitable carrier or excipient as in combined therapy.

In addition, the pharmaceutical composition for the preventing or treating bacterial infectious disease containing the Romo1-derived peptide and/or a variant thereof as an active ingredient according to the present invention may be formulated and used in the form of powder, granules, tablets, capsules, suspensions, emulsions, syrups, external preparations such as aerosols, and sterile injection solutions, according to respective conventional method. The antibacterial composition of the present invention may be administered orally or parenterally (e.g., intravenously, subcutaneously, intraperitoneally or topically) according to a desired method. The dosage thereof varies depending on the patient's condition and weight, the severity of the disease, the form of drug, and the route and duration of administration, but may be appropriately selected by those skilled in the art. For example, the antibacterial composition may be administered in an amount of about 0.001 mg to 1,000 mg in combination with a pharmaceutically acceptable carrier. The antibacterial composition of the present invention may be administered once or several times a day as needed, and it may be used alone or in combination with surgery, hormone therapy, drug therapy, and methods using biological response modifiers.

In addition, the Romo1-derived peptide and/or a variant thereof according to the present invention may provide a quasi-drug composition for the purpose of preventing or ameliorating bacterial infectious disease. The quasi-drug composition of the present invention may be used together with other quasi-drugs or quasi-drug components, and it may be appropriately used according to a conventional method. The quasi-drug composition may be used in, but not limited to, a disinfectant cleanser, shower foam, mouthwash, wet tissue, detergent soap, hand wash, humidifier filler, mask, ointment, or filter filler.

In addition, the Romo1-derived peptide and/or a variant thereof according to the present invention may be provided in the form of a cosmetic composition. The formulation of the cosmetic composition according to the present invention may be in the form of skin lotion, skin softener, skin toner, astringent, lotion, milk lotion, moisture lotion, nourishing lotion, massage cream, nourishing cream, moisture cream, hand cream, foundation, essence, nourishing essence, pack, soap, cleansing foam, cleansing lotion, cleansing cream, body lotion, or body cleanser. The cosmetic composition of the present invention may be combined with other ingredients that are commonly used in cosmetics, if necessary, in addition to containing the above essential ingredients.

In addition, the present invention provides a food composition or feed composition containing the Romo1-derived peptide and/or a variant thereof as an active ingredient. When the Romo1-derived peptide and/or a variant thereof according to the present invention is used as an additive to food or feed, the Romo1-derived peptide and/or a variant thereof may be added as it is or used together with other food, feed, or components thereof, and may be used appropriately according to a conventional method. The content of the active ingredient in the composition may be suitably determined depending on the intended use (prophylactic or therapeutic treatment of infectious diseases by inhibition of proliferation and growth of bacteria, or health treatment). In general, in the production of feed, food or beverages, the Romo1-derived peptide and/or a variant thereof according to the present invention is added in an amount of 15 wt % or less, preferably 10 wt % or less, based on the total weight of raw materials. However, in the case of long-term intake for the purpose of health and hygiene or health control, the amount may be smaller than the lower limit of the above range, and the active ingredient may be used in an amount larger than the upper limit of the above range because it is not problematic in terms of safety. There is no particular limitation on the type of the food and feed.

In the present invention, amino acids are abbreviated as follows according to the IUPAC-IUB nomenclature.

Arginine (Arg, R), lysine (Lys, K), histidine (His, H), serine (Ser, S), threonine (Thr, T), glutamine (Gln, Q), asparagine (Asp, N), methionine (Met, M), leucine (Leu, L), isoleucine (Ile, I), valine (Val, V), phenylalanine (Phe, F), tryptophan (Trp, W), tyrosine (Tyr, Y), alanine (Ala, A), glycine (Gly, G), proline (Pro, P), cysteine (Cys, C), aspartic acid (Asp, D), glutamic acid (Glu, E), and norleucine (Nle).

Although the present invention may be modified variously and have several embodiments, specific embodiments are illustrated in the accompanying drawings and will be described in detail in the detailed description. However, it should be understood that the present invention is not limited to the specific embodiments and includes all the changes, equivalents and replacements included in the spirit and scope of the present invention. In the following description, the detailed description of related publicly-known technology will be omitted when it may obscure the subject matter of the present invention.

EXAMPLES

Example 1. Evaluation of Antibacterial Activities of Romo1-Derived Peptides and Identification of Optimal Peptides Romo1 protein comprises two α-helices. The present inventors synthesized the α-helix 2 region having both hydrophilicity and hydrophobicity, and evaluated the antibacterial activity thereof using minimum bactericidal concentration (MBC) assay. The α-helix 2 region was named KU-5279 (the 52-79 amino acid region of Romo1 protein). Then, in order to identify peptides that are beneficial for human application and have excellent antibacterial activity, the present inventors synthesized several peptides comprising a sequence of contiguous amino acids starting at any amino acid selected from the 52-79 amino acid region of Romo1 protein, and comparatively evaluated the antibacterial activities of the peptides by minimum bactericidal concentration assay (See Table 1 below for information on each peptide). Evaluation of the antibacterial activity of each peptide by minimum bactericidal concentration assay was specifically performed as follows.

First, each of *Pseudomonas aeruginosa* (ATCC 27853) and *Staphylococcus aureus* (ATCC 29213) was cultured in 3% (w/v) TSB (Tryptic Soy Broth) liquid medium at 37° C. and 200 rpm for 4 hours, and then further cultured under the same conditions for 3 hours to a concentration of $5 \times 10^6$ CFU/ml. Strain solutions were prepared by diluting each of the further cultured strains with SP (sodium phosphate; 10 mM sodium phosphate, 1% TSB) buffer to a final concentration of $2 \times 10^5$ CFU/ml.

Then, each peptide at varying concentrations (0 μg/ml to 300 μg/ml) was dispensed into each well of a 96-well microplate, and 100 μl ($1 \times 10^5$ CFU/ml) of each of the prepared strain solutions was added thereto, mixed therewith, and allowed to react with the peptide in an incubator at 37° C. for 1 hour.

In addition, 30 g/L of TS (tryptic soy) and 15 g/L of agar were dissolved in distilled water and sterilized, and then 25 ml of the solution was poured onto a 100 mm round plate and solidified at room temperature for one day or more, thereby preparing a TS agar plate. 10 μl of each reaction solution of the peptide and the strain was plated on the TS agar plate at a constant size, and incubated in an incubator at 37° C. for 18 hours, and then colony formation on the plate was checked. The minimum bactericidal concentration was defined as the minimum concentration of the peptide at which no colony was formed, and the experimental results are shown in Table 1 below.

TABLE 1

| SEQ ID NO | Peptide | Amino acid sequence | MBC value (μg/ml) against *Staphylococcus aureus* | MBC value (μg/ml) against *Pseudomonas aeruginosa* |
|---|---|---|---|---|
| 1 | Romo1 | MPVAVGPYGQSQPSCFDRVKMGFVMGCAVGMAAGALFGTFSCLRIGMRGRELMGGIGKTMMQSGGTFGTFMAIGMGIRC | Insoluble | Insoluble |
| 2 | KU-5278 | LMGGIGKTMMQSGGTFGTFMAIGMGIR | 300 | 300 |
| 3 | KU-5279 | LMGGIGKTMMQSGGTFGTFMAIGMGIRC | 300 | 300 |
| 4 | KU-5478 | GGIGKTMMQSGGTFGTFMAIGMGIR | 300 | 300 |
| 5 | KU-5479 | GGIGKTMMQSGGTFGTFMAIGMGIRC | 200 | 300 |
| 6 | KU-5678 | IGKTMMQSGGTFGTFMAIGMGIR | 300 | 300 |
| 7 | KU-5679 | IGKTMMQSGGTFGTFMAIGMGIRC | 300 | 300 |
| 8 | KU-5778 | GKTMMQSGGTFGTFMAIGMGIR | 280 | 300 |
| 9 | KU-5779 | GKTMMQSGGTFGTFMAIGMGIRC | 250 | 280 |
| 10 | KU-5875 | KTMMQSGGTFGTFMAIGM | >300 | >300 |
| 11 | KU-5876 | KTMMQSGGTFGTFMAIGMG | >300 | >300 |
| 12 | KU-5877 | KTMMQSGGTFGTFMAIGMGI | >300 | >300 |
| 13 | KU-5878 | KTMMQSGGTFGTFMAIGMGIR | 100 | 100 |
| 14 | KU-5879 | KTMMQSGGTFGTFMAIGMGIRC | 150 | 150 |
| 15 | KU-6079 | MMQSGGTFGTFMAIGMGIRC | >300 | >300 |

TABLE 1-continued

| SEQ ID NO | Peptide | Amino acid sequence | MBC value (μg/ml) against Staphylococcus aureus | MBC value (μg/ml) against Pseudomonas aeruginosa |
|---|---|---|---|---|
| 48 | pCM19 | CLRIGMRGRELMGGIGKTM | 250 | 300 |
| 49 | pCM12 | CLRIGMRGRELM | >300 | >300 |

As shown in Table 1, the pCM19 and KU-5279 peptides showed similar bactericidal activities, but pCM12 had low bactericidal activity, and hence it was impossible to measure the antibacterial activity thereof using the minimum bactericidal concentration assay. Meanwhile, it could be confirmed that the KU-5878 peptide consisting of 21 amino acid residues had the best antibacterial activity, and it was confirmed that KU-5878 had three times better antibacterial activity than KU-5279.

Example 2. Evaluation of Antibacterial Activity of KU-5878

2-1. Evaluation of Antibacterial Activity Against Various Bacteria

In order to identify the type of bacteria against which the peptide comprising the 52-79 amino acid region of the Romo1 protein or a portion of the region and confirmed to have antibacterial activity in Example 1 exhibits bactericidal activity, KU-5878 was selected as a representative among the synthetic peptides shown in Table 1 above, and the antibacterial activities thereof against the bacteria shown in Table 2 below were measured using minimum bactericidal concentration assay. The minimum bactericidal concentration assay was the same as the method used in Example 1.

Specifically, each type of bacteria was cultured in 3% (w/v) TSB (Tryptic Soy Broth) liquid medium at 37° C. and 200 rpm for 4 hours, and then further cultured under the same conditions for 3 hours to a concentration of 5×10$^6$ CFU/ml. Strain solutions were prepared by diluting each of the further cultured with strains SP buffer a final to concentration of 2×10$^5$ CFU/ml.

Then, the KU-5878 peptide at varying concentrations (0 μg/ml to 300 μg/ml) was dispensed into each well of a 96-well microplate, and 100 μl (1×10$^5$ CFU/ml) of each of the prepared strain solutions was added thereto, mixed therewith, and allowed to react with the peptide in an incubator at 37° C. for 1 hour.

In addition, 10 μl of each reaction solution of the peptide and the strain was plated on the TS agar plate at a constant size, and incubated in an incubator at 37° C. for 18 hours, and then colony formation on the plate was checked. The minimum bactericidal concentration was defined as the minimum concentration of the peptide at which no colony was formed, and the experimental results are shown in Table 2 below.

Meanwhile, the multidrug-resistant *Pseudomonas aeruginosa*, multidrug-resistant *Acinetobacter* and multidrug-resistant *Klebsiella* in Table 2 below were bacteria isolated from patients at Korea University Anam Hospital. It was confirmed that multidrug-resistant *Pseudomonas aeruginosa* had resistance to piperacillin, piperacillin-tazobactam, ceftazidime, imipenem, meropenem, gentamicin, amikacin, and ciprofloxacin antibiotics, the multidrug-resistant *Acinetobacter* had resistance to piperacillin, piperacillin-tazobactam, ceftazidime, imipenem, meropenem, gentamicin, amikacin, ciprofloxacin, and cefepime antibiotics, and the multidrug-resistant *Klebsiella* had resistance to piperacillin-tazobactam, ceftazidime, cefepime, imipenem, gentamicin, and ciprofloxacin antibiotics. Then, these bacteria were used in the experiment.

TABLE 2

| Group | Bacteria that cause sepsis and pneumonia and multidrug-resistant bacteria | Accession No. | MBC value (μg/ml) of KU-5878 |
|---|---|---|---|
| Gram-positive | Staphylococcus aureus | ATCC 29213 | 100 |
| | Bacillus subtilis | ATCC 6633 | 90 |
| | Enterococcus faecium | ATCC 19434 | 85 |
| | Streptomyces sindenensis | ATCC 12392 | 95 |
| | Enterococcus faecalis | ATCC 19433 | 85 |
| | Streptococcus pneumoniae | NCCP 14585 | 100 |
| Gram-negative | Escherichia coli | ATCC 25922 | 85 |
| | Klebsiella pneumoniae | ATCC 13883 | 100 |
| | Acinetobacter baumannii | ATCC 19606 | 100 |
| | Pseudomonas aeruginosa | ATCC 27853 | 100 |
| | Enterobacter aerogenes | ATCC 13048 | 90 |
| Multidrug-resistant bacteria | Methicillin-resistant *S. aureus* | ATCC 33591 | 100 |
| | Multidrug-resistant *P. aeruginosa* | — | 110 |
| | Multidrug-resistant *A. baumannii* | — | 110 |
| | Multidrug-resistant *K. pneumoniae* | — | 100 |
| | Vancomycin-resistant *E. faecium* | NCCP 11522 | 100 |
| | Vancomycin-resistant *S. aureus* | NCCP 15872 | 120 |

As shown in Table 2 above, it could be seen that KU-5878 exhibited a broad spectrum of antibacterial activity against all the gram-positive bacteria, gram-negative bacteria and multidrug-resistant bacteria.

2-2. Comparative Evaluation of Antibacterial Activity of KU-5878 with Those of Known Antimicrobial Peptides In order to confirm whether the KU-5878 peptide confirmed to have antibacterial activity in vitro effectively exhibits bactericidal activity against bacteria in vivo, especially in the blood vessels of animals, *Staphylococcus aureus* as gram-positive bacteria, *Pseudomonas aeruginosa* as gram-negative bacteria, methicillin-resistant *Staphylococcus aureus* and multidrug-resistant *Pseudomonas aeruginosa* as multidrug-resistant bacteria were selected as representatives, and the following experiment was performed.

Specifically, *Staphylococcus aureus, Pseudomonas aeruginosa*, methicillin-resistant *Staphylococcus aureus* and multidrug-resistant *Pseudomonas aeruginosa* was cultured in 3% (w/v) TSB liquid medium at 37° C. and 200 rpm for 4 hours, and then further cultured under the same conditions for 3 hours to a concentration of $5 \times 10^9$ CFU/ml. Strain solutions were prepared by diluting each of the further cultured strains with PBS solution to a final concentration of $1 \times 10^5$ CFU/μl.

Next, 100 μl of each strain solution was injected intravenously (IV) into the tail vein of each of 10-week-old male mice (C57BL/6). After one hour, KU-5878 was intravenously injected at a concentration of 10 mg/kg. As a control, PBS was intravenously injected at a concentration of 10 mg/kg, and as a positive control, LL-37, magainin 2, or daptomycin was intravenously injected at a concentration of 10 mg/kg.

40 minutes after the intravenous injection of each drug, about 1 cm from the tail end of each mouse was cut using surgical scissors, and 10 μl of the blood at the end of the cut was collected and diluted in PBS. The diluted blood sample was plated on a previously prepared TSB agar plate and incubated in an incubator at 37° C. for 18 hours, and the formed colonies were counted for comparison.

Figure 2:
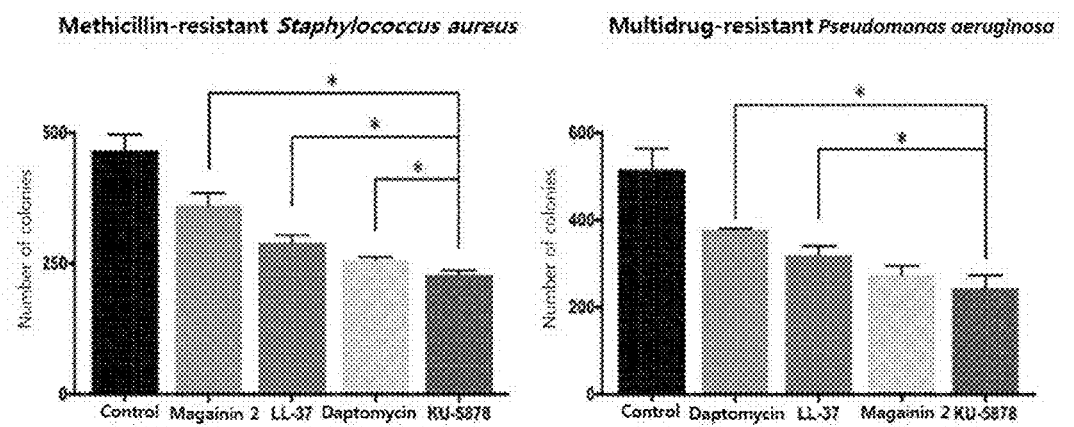
FIG. 2 shows the results of comparing the antibacterial activity of KU-5878 with those of conventional antimicrobial peptides (LL-37, magainin 2, and daptomycin) against multidrug-resistant bacteria.

As a result, as shown in FIGS. 1 and 2, it could be seen that the number of bacteria remaining in the blood vessels of the mice was decreased by intravenous injection of the drug, and was most greatly decreased when KU-5878 was administered. Thereby, it could be seen that KU-5878 exhibits significantly better antibacterial activity than LL-37, magainin 2 and daptomycin, which are known to have antibacterial activity.

2-2. Comparative Evaluation of Antibacterial Activity of KU-5878 with Those of Known Antibiotics Following Example 2-2, in order to evaluate the antibacterial activity of KU-5878 peptide in vivo, *Staphylococcus aureus* as gram-positive bacteria, *Pseudomonas aeruginosa, Klebsiella pneumoniae* and *Acinetobacter baumannii* as gram-negative bacteria, and multidrug-resistant *Pseudomonas aeruginosa*, methicillin-resistant *Staphylococcus aureus*, multidrug-resistant *Klebsiella pneumoniae* and multidrug-resistant *Acinetobacter baumannii* as multidrug-resistant bacteria were selected, and the following experiment was performed.

The experimental method is as described in Example 2-2 above. However, the final concentration of each strain administered to mice is shown in Table 3 below. For a positive group, each type of the bacteria was injected into mice, and after 24 hours, 30 mg/kg of imipenem, a carbapenem-based antibiotic, was injected intraperitoneally (IP), and then the same amount of imipenem was administered intraperitoneally a total of 4 times at 12-hour intervals. The survival rates of each control group and the experimental group were measured at 24-hour intervals.

TABLE 3

| Bacteria | Final concentration (CFU) |
|---|---|
| *Staphylococcus aureus* | $1 \times 10^8$ |
| *Pseudomonas aeruginosa* | $2 \times 10^7$ |
| *Klebsiella pneumoniae* | $8 \times 10^8$ |
| *Acinetobacter baumannii* | $4 \times 10^8$ |
| Methicillin-resistant *Staphylococcus aureus* | $3 \times 10^8$ |
| Multidrug-resistant *Pseudomonas aeruginosa* | $8 \times 10^7$ |
| Multidrug-resistant *Acinetobacter baumannii* | $5 \times 10^8$ |
| Multidrug-resistant *Klebsiella pneumoniae* | $8 \times 10^8$ |

Figure 3:
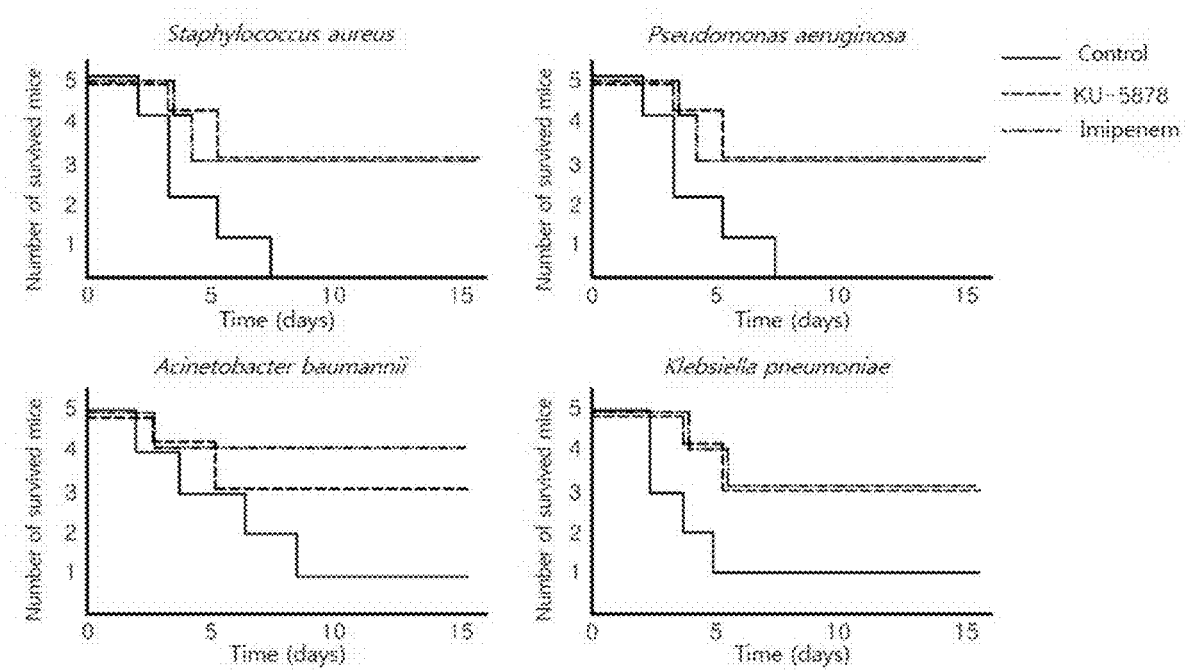
FIG. 3 shows the results of comparing the antibacterial activity of KU-5878 with that of a conventional antibiotic (imipenem) against gram-positive and gram-negative bacteria.
Figure 4:
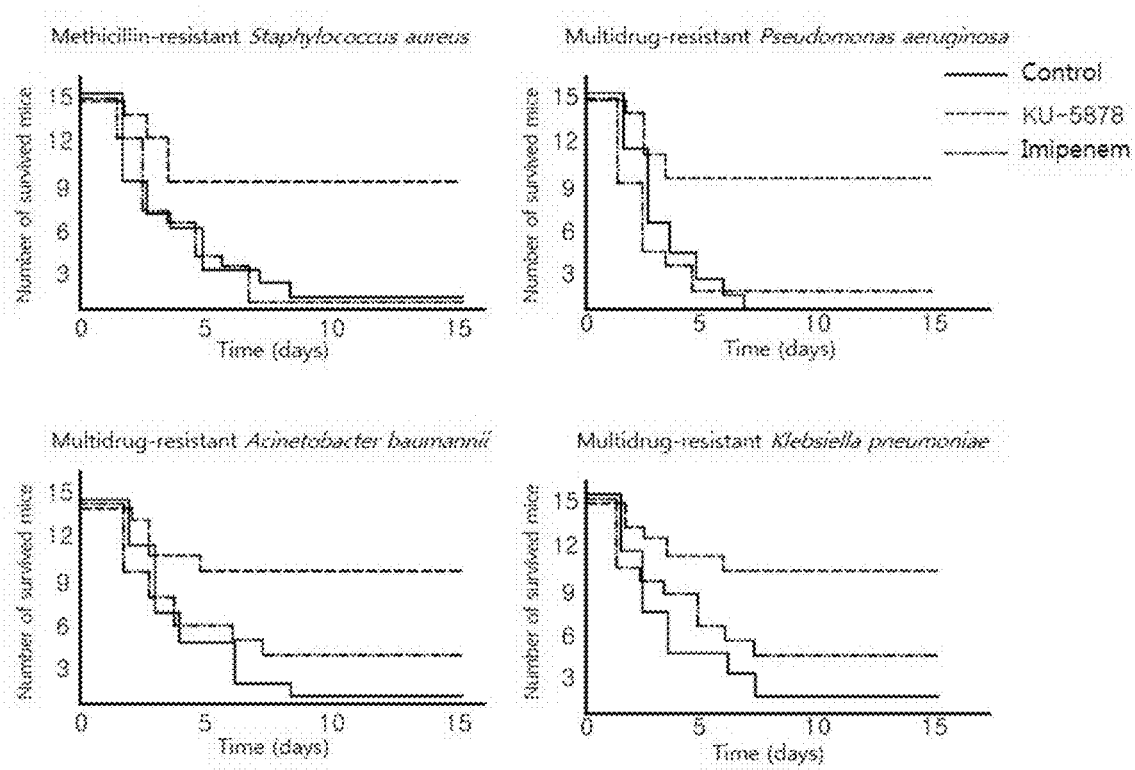
FIG. 4 shows the results of comparing the antibacterial activity of KU-5878 with that of a conventional antibiotic (imipenem) against multidrug-resistant bacteria.

As a result, as shown in FIG. 3, the survival rate of the mice injected with only the gram-positive or gram-negative bacteria was 0 to 20%, the survival rate of the mice injected with KU-5878 was 60%, and the survival rate of the mice injected with imipenem was about 60 to 80%. In addition, as can be seen in FIG. 4, the mice injected with only multidrug-resistant bacteria showed a survival rate of 0 to 7%, the mice injected with KU-5878 showed a survival rate of 60 to 67%, and the mice injected with imipenem showed a survival rate of 7 to 27%.

Example 3. Evaluation of Toxicity of KU-5878

In order to confirm whether the peptide comprising the 52-79 amino acid region of the Romo1 protein or a portion of the region and confirmed to have bactericidal activity against the gram-positive, gram-negative and multidrug-resistant bacteria in Examples 1 and 2 is applicable to a subject, the toxicity of the peptide was measured. In the following experiment, KU-5878 was selected as a representative among the synthetic peptides shown in Table 1, and the toxicity of KU-5878 was evaluated.

3-1. Evaluation Toxicity to Human Vascular Endothelial Cells (HUVECs)

Human vascular endothelial cells (HUVECs) were cultured in a 96-well microplate, and MTT (3-(4,5-dimethylthiazol-2-yl)-2,5-diphenyltetrazolium bromide) reagent was dissolved in PBS at a concentration of 2 mg/ml and then sterile-filtered through a 0.2-μm membrane filter. PBS was used as a control.

The HUMEC medium was replaced with fresh medium, and KU-5878, melittin or magainin 2 were dispensed at various concentrations (0 μg/ml to 300 μg/ml). Then, each well was treated with 100 μl of MTT reagent and incubated at 37° C. for 2 hours. Then, the medium and the peptide were carefully removed so as not to separate the cells, and 100 μl of DMSO (dimethyl sulfoxide) was added to each well, and the absorbance at a wavelength of 570 nm was measured using a spectrophotometer. Relative cell viability was calculated as a percentage of the viability of untreated control cells.

Figure 5:
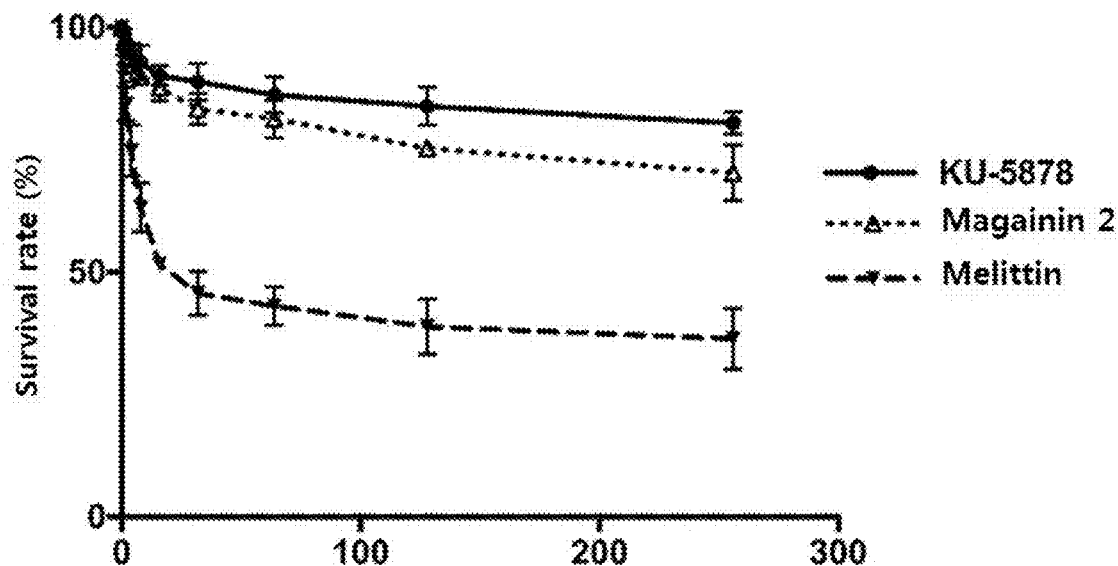
FIG. 5 shows the results of comparing the cytotoxicity of KU-5878 with those of conventional antimicrobial peptides (magainin 2 and melittin) to human vascular endothelial cells (HUVECs).

As a result, as shown in FIG. 5, it could be seen that KU-5878 showed very low toxicity to the HUVECs.

3-2. Evaluation of Toxicity to Red Blood Cells

Red blood cells were diluted with PBS, centrifuged 3 times at 900 g for 10 minutes, and washed. 100 μl of the diluted red blood cell solution (10% v/v PBS) was dispensed into each well of a 96-well microplate, and KU-5878, KU-5878-K4, KU-5878-K4-D, melittin, magainin 2 or daptomycin was added to each well which was then filled with PBS to 200 μl, followed by reaction by incubation at 37° C. for 1 hour. Then, the supernatant of the reaction solution was separated, and the absorbance at a wavelength of 550 nm was measured using a spectrophotometer. As control, PBS and 0.1% Triton X-100 (Triton X-100) solution were used.

Figure 6:
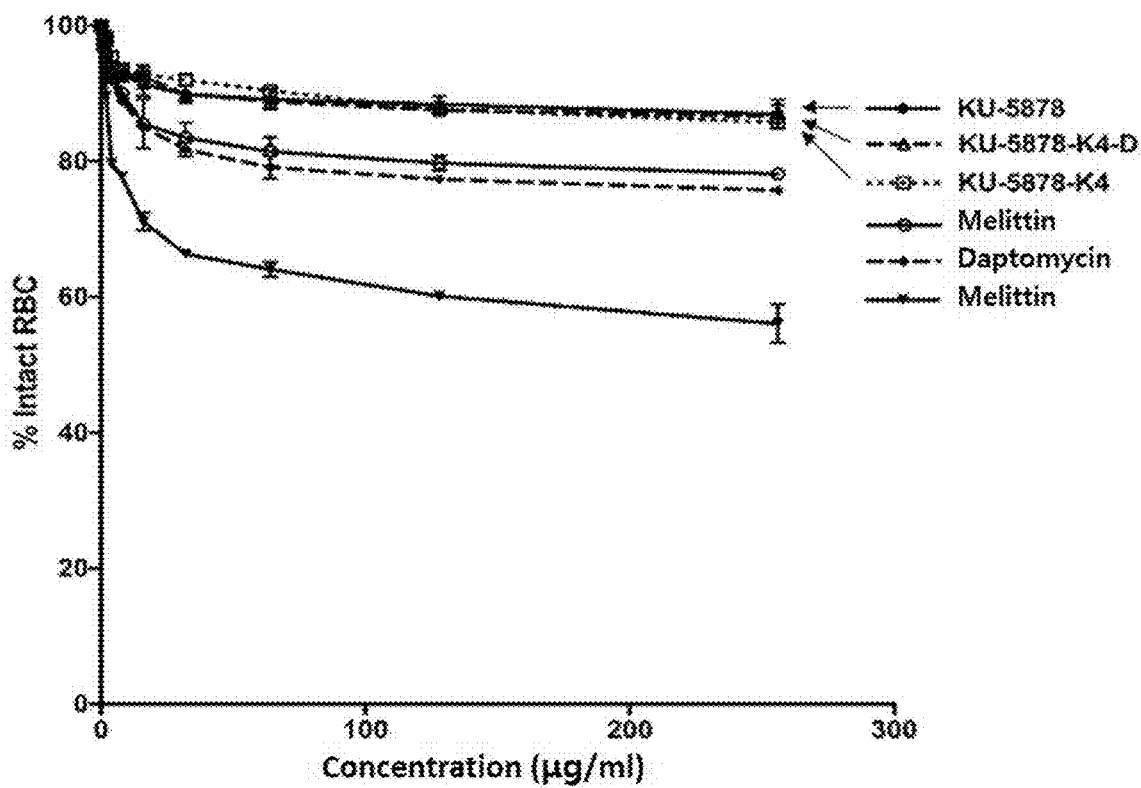
FIG. 6 shows the results of comparing the cytotoxicities of KU-5878 and KU-5878 variants (KU-5878-K4 and KU-5878-K4-D) with those of conventional antimicrobial peptides (LL-37, magainin 2, and melittin) to mouse red blood cells by the degree of red blood cell hemolysis.

Based on the results of measurement of the absorbance, the degree of red blood cell destruction was calculated according to Equation 1 below, and the results of the calculation are shown in FIG. 6.

The % intact RBC=100(%)−[(absorbance of peptide-treated red blood cell solution−absorbance of PBS-treated red blood cell solution)/(absorbance of Triton X-100-treated red blood cell solution−absorbance of PBS-treated red blood cell solution)×100(%)]   [Equation 1]

As a result, as shown in FIG. 6, it was confirmed that KU-5878 showed little hemolysis even at a high concentration. Like KU-5878, KU-5878-K4 and KU-5878-K4-D also showed little hemolysis of red blood cells compared to magainin 2, daptomycin and melittin, suggesting that they have very low toxicity to red blood cells.

3-3. Evaluation of Toxicity In Vivo

In order to evaluate whether the KU-5878 peptide confirmed to be non-toxic in vitro does not show toxicity to a subject in vivo, especially when injected into the blood vessels of animals (subject), KU-5878 was injected intravenously into the tail vein of each 10-week-old male mouse (C57BL/6) at a concentration of 100 mg/kg. At this time, the maximum volume of the injection dose was 150 μl. The behavior of the mice was observed for 1 hour after injection, and then changes in the weights of the mice were measured at 24-hour intervals for 12 days.

Figure 7:
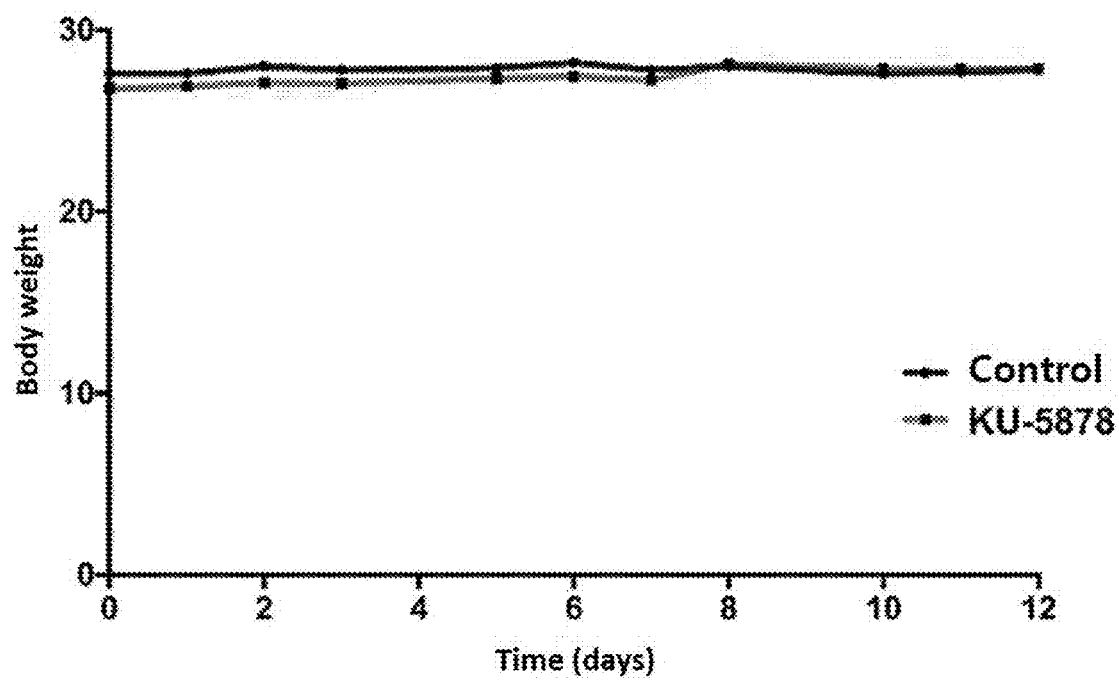
FIG. 7 shows the results of observing the weights of mice to confirm the non-toxicity of KU-5878 in vivo.

As a result, it could be confirmed that the mice to which KU-5878 was administered all survived, and KU-5878 had no effect on the weight of the mice as shown in FIG. 7.

Example 4. Evaluation of Antibacterial Activities of Peptides in Which Some of Amino Acids Constituting KU-5878 are Substituted 4-1. Evaluation of Antibacterial Activity of KU-5878 Variants Comprising Amino Acid Sequence of SEQ ID NO: 16

Next, in order to identify a peptide with better antibacterial activity, the hydrophilic amino acid residues of KU-5878 were substituted with positively charged lysine (K) or arginine (R), and then the antibacterial activities of the variants were comparatively evaluated using minimum bactericidal concentration assay. The experiment was performed in the same manner as in Example 1. Specific information on the KU-5878 variants and the MBC values thereof against each bacterium are shown in Table 4 below.

TABLE 4

| SEQ ID NO | Peptide | Amino acid sequence | MBC value (μg/ml) against *Staphylococcus aureus* | MBC value (μg/ml) against *Pseudomonas aeruginosa* | MBC value (μg/ml) against methicillin-resistant *Staphylococcus aureus* | MBC value (μg/ml) against multidrug-resistant *Pseudomonas aeruginosa* |
|---|---|---|---|---|---|---|
| 13 | KU-5878 | KTMMQSGGTFGTFMAIGMGIR | 100 | 100 | 100 | 110 |
| 17 | KU-5878-T59K | KKMMQSGGTFGTFMAIGMGIR | 40 | 50 | 45 | 45 |
| 18 | KU-5878-Q62K | KTMMKSGGTFGTFMAIGMGIR | 80 | 90 | 85 | 90 |
| 19 | KU-5878-S63K | KTMMQKGGTFGTFMAIGMGIR | 50 | 60 | 60 | 60 |
| 20 | KU-5878-T66K | KTMMQSGGKFGTFMAIGMGIR | 60 | 80 | 70 | 80 |
| 21 | KU-5878-T69K | KTMMQSGGTFGKFMAIGMGIR | 130 | 140 | 150 | 150 |
| 22 | KU-5878-K2 (T59K, Q62K) | KKMMKSGGTFGTFMAIGMGIR | 8 | 8 | 8 | 8 |
| 23 | KU-5878-K3 (T59K, Q62K, S63K) | KKMMKKGGTFGTFMAIGMGIR | 4 | 4 | 5 | 4 |
| 24 | KU-5878-K4 (T59K, Q62K, S63K, T66K) | KKMMKKGGKFGTFMAIGMGIR | 3 | 4 | 5 | 5 |
| 25 | KU-5878-K58R | RTMMQSGGTFGTFMAIGMGIR | 120 | 120 | 130 | 120 |
| 26 | KU-5878-K58A | ATMMQSGGTFGTFMAIGMGIR | >300 | >300 | >300 | >300 |
| 27 | KU-5878-T59R | KRMMQSGGTFGTFMAIGMGIR | 25 | 30 | 30 | 35 |

TABLE 4-continued

| SEQ ID NO | Peptide | Amino acid sequence | MBC value (μg/ml) against Staphylococcus aureus | MBC value (μg/ml) against Pseudomonas aeruginosa | MBC value (μg/ml) against methicillin-resistant Staphylococcus aureus | MBC value (μg/ml) against multidrug-resistant Pseudomonas aeruginosa |
|---|---|---|---|---|---|---|
| 28 | KU-5878-R78A | KTMMQSGGTFGTFMAIGMGI<u>A</u> | >300 | >300 | >300 | >300 |
| 29 | KU-5878-R78K | KTMMQSGGTFGTFMAIGMGI<u>K</u> | >300 | >300 | >300 | >300 |

As can be seen in Table 4, it could be seen that the peptide, obtained by substituting lysine for the amino acid at position 59, 62, 63 or 66 of the Romo1 protein, and the peptide obtained by substituting arginine for the amino acid at position 59, had better antibacterial activity than KU-5878. In addition, it could be confirmed that the KU-5878 variant obtained by substituting arginine for the amino acid at position 58 of the Romo1 protein also showed antibacterial activity similar to that of KU-5878.

From the above results, it can be seen that, even when the hydrophilic amino acid in the α-helix 2 region of the Romo1 protein is substituted with a positively charged amino acid, particularly lysine (K) or arginine (R), the peptide can exhibit similar antibacterial activity or better antibacterial activity.

4-2. Evaluation of Antibacterial Activity of KU-5878-K4 Against Various Bacteria In order to identify the type of bacteria against which the KU-5878 variants confirmed to have antibacterial activity in Example 4-1 exhibit bactericidal activity, KU-5878-K4 was selected as a representative among the KU-5878 variants shown in Table 4 above, and the antibacterial activities thereof against the bacteria shown in Table 5 below were measured using minimum bactericidal concentration assay. The minimum bactericidal concentration assay was performed in the same manner as in Example 1.

As can be seen in Table 5 above, it could be seen that KU-5878-K4 exhibited a broad spectrum of antibacterial activity against all the gram-positive bacteria, gram-negative bacteria and multidrug-resistant bacteria.

4-3. Evaluation of Antibacterial Activities of KU-5878 Variants Comprising Amino Acid Sequence of SEQ ID NO: 30

In Example 4-1, it was confirmed that, even when the hydrophilic residue of KU-5878 was substituted with a positively charged amino acid, the antibacterial activity thereof was maintained or better antibacterial activity was exhibited. Then, methionine (M) or isoleucine (I) in KU-5878, which is hydrophobic and has a similar residue structure, was substituted with a hydrophilic amino acid or an amino acid having a different residue structure, and then the antibacterial activities of the variants were comparatively evaluated using minimum bactericidal concentration assay. The experiment was performed in the same manner as in Example 1. Specific information on the KU-5878 variants and the MBC values thereof against each bacterium are shown in Table 6 below.

TABLE 5

| Group | Bacteria that cause sepsis and pneumonia and multidrug-resistant bacteria | Accession number | MBC value of (μg/ml) of KU-5878-K4 |
|---|---|---|---|
| Gram positive | Staphylococcus aureus | ATCC 29213 | 3 |
| | Bacillus subtilis | ATCC 6633 | 5 |
| | Enterococcus faecium | ATCC 19434 | 5 |
| | Streptomyces sindenensis | ATCC 12392 | 5 |
| | Enterococcus faecalis | ATCC 19433 | 5 |
| | Streptococcus pneumoniae | NCCP 14585 | 4 |
| Gram negative | Escherichia coli | ATCC 25922 | 5 |
| | Klebsiella pneumoniae | ATCC 13883 | 5 |
| | Acinetobacter baumannii | ATCC 19606 | 4 |
| | Pseudomonas aeruginosa | ATCC 27853 | 4 |
| | Enterobacter aerogenes | ATCC 13048 | 5 |
| Multi drug-resistant bacteria | Methicillin-resistant S. aureus | ATCC 33591 | 5 |
| | Multidrug-resistant P. aeruginosa | — | 5 |
| | Multidrug-resistant A. baumannii | — | 4 |
| | Multidrug-resistant K. pneumoniae | — | 5 |
| | Vancomycin-resistant E. faecium | NCCP 11522 | 5 |
| | Vancomycin-resistant S. aureus | NCCP 15872 | 6 |

TABLE 6

| SEQ ID NO | Peptide | Amino acid sequence | MBC value (μg/ml) against Staphylococcus aureus | MBC value (μg/ml) against Pseudomonas aeruginosa |
|---|---|---|---|---|
| 31 | KU-5878-M60A | KT<u>A</u>MQSGGTFGTFMAIGMGIR | >300 | >300 |
| 32 | KU-5878-I73A | KTMMQSGGTFGTFMA<u>A</u>GMGIR | >300 | >300 |
| 33 | KU-5878-I73K | KTMMQSGGTFGTFMA<u>K</u>GMGIR | >300 | >300 |
| 34 | KU-5878-I73W | KTMMQSGGTFGTFMA<u>W</u>GMGIR | 300 | 300 |
| 35 | KU-5878-I77A | KTMMQSGGTFGTFMAIGMG<u>A</u>R | >300 | >300 |
| 36 | KU-5878-I77K | KTMMQSGGTFGTFMAIGMG<u>K</u>R | >300 | >300 |
| 37 | KU-5878-I77T | KTMMQSGGTFGTFMAIGMG<u>T</u>R | >300 | >300 |
| 38 | KU-5878-I77G | KTMMQSGGTFGTFMAIGMG<u>G</u>R | 90 | 80 |
| 39 | KU-5878-4Nle | KT(Nle)(Nle)QSGGTFGTF(Nle)AIG(Nle)GIR | 90 | 110 |

As can be seen in Table 6 above, when methionine or isoleucine in KU-5878, which is hydrophobic and has a similar residue structure, was substituted with a hydrophilic amino acid, the antibacterial activity of the peptide decreased. On the other hand, when methionine was substituted with norleucine (Nle) having a similar residue structure, the change in the antibacterial activity of the peptide was not significant. In addition, it could be seen that, when isoleucine was substituted with glycine (G), the antibacterial activity of the peptide increased.

4-4. Evaluation of Antibacterial Activities of KU-5878 Variants Comprising Amino Acid Sequence of SEQ ID NO: 40

Next, in order to identify a KU-5878 variant having antibacterial activity comparable to or higher than that of KU-5878, phenylalanine (F) in KU-5878, which is hydrophobic, was substituted with a hydrophilic amino acid or an amino acid having a different residue structure, and then the antibacterial activities of the variants were comparatively evaluated using minimum bactericidal concentration assay. The experiment was performed in the same manner as in Example 1. Specific information on the KU-5878 variants and the MBC values thereof against each bacterium are shown in Table 7 below.

As a result, as can be seen in Table 7 above, it could be seen that, when phenylalanine at position 67 in KU-5878, which is hydrophobic, was substituted with tryptophan having a similar residue structure, the antibacterial activity of the peptide increased.

4-5. Evaluation of Antibacterial Activities of KU-5878 Variants Comprising Amino Acid Sequence of SEQ ID NO: 45

Following Example 4-4, alanine (A) or glycine (G) in KU-5878 was substituted with glycine or alanine, and then the antibacterial activities of the variants were comparatively evaluated using minimum bactericidal concentration assay. The experiment was performed in the same manner as in Example 1. Specific information on the KU-5878 variants and the MBC values thereof against each bacterium are shown in Table 8 below.

TABLE 7

| SEQ ID NO | Peptide | Amino acid sequence | MBC value (μg/ml) against Staphylococcus aureus | MBC value (μg/ml) against Pseudomonas aeruginosa |
|---|---|---|---|---|
| 41 | KU-5878-F67A | KTMMQSGGT<u>A</u>GTFMAIGMGIR | >300 | >300 |
| 42 | KU-5878-F67W | KTMMQSGGT<u>W</u>GTFMAIGMGIR | 80 | 80 |
| 43 | KU-5878-F70K | KTMMQSGGTAGT<u>K</u>MAIGMGIR | >300 | >300 |
| 44 | KU-5878-F70W | KTMMQSGGTAGT<u>W</u>MAIGMGIR | 300 | 300 |

TABLE 8

| SEQ ID NO | Peptide | Amino acid sequence | MBC value (µg/ml) against Staphylococcus aureus | MBC value (µg/ml) against Pseudomonas aeruginosa |
|---|---|---|---|---|
| 46 | KU-5878-A72G | KTMMQSGGTFGTFMGIGMGIR | 350 | 350 |
| 47 | KU-5878-G76A | KTMMQSGGTFGTFMAIGMAIR | >400 | >400 |

As a result, as can be seen in Table 8 above, it could be seen that the peptide obtained by substituting glycine for alanine or substituting alanine for glycine in KU-5878 showed antibacterial activity, but showed decreased antibacterial activity compared to that of the KU-5878.

4-6. Evaluation of Antibacterial Activities of Peptides in which Some or all of Amino Acids Constituting KU-5878 and KU-5878-K4 are Substituted with D-Amino Acids Following Example 4-5, peptides (KU-5878-D (all) and KU-5878-K4-D) were synthesized by substituting D-amino acids for the amino acids constituting KU-5878 and KU-5878-K4, and the antibacterial activities thereof were comparatively evaluated. KU-5878-K4-D is a peptide obtained by substituting D-amino acids for the lysine amino acid residues at positions 59, 62, 63 and 66 in KU-5878-K4, and KU-5878-D (all) is a peptide obtained by substituting D-amino acids for all the amino acids of KU-5878.

Measurement of the maximum bactericidal concentration of each of the peptides in the presence or absence of bovine serum was performed in the same manner as in Example 1, and the results are shown in Table 9 below.

TABLE 9

| | Bovine serum X | | Bovine serum O | |
|---|---|---|---|---|
| Peptide name | MBC (µg/ml) value against Staphylococcus aureus | MBC (µg/ml) value against Pseudomonas aeruginosa | MBC (µg/ml) value against Staphylococcus aureus | MBC (µg/ml) value against Pseudomonas aeruginosa |
| KU-5878 | 100 | 100 | 300 | 300 |
| KU-5878-D(all) | 300 | 300 | >500 | >500 |
| KU-5878-K4 | 3 | 4 | 40 | 32 |
| KU-5878-K4-D | 3 | 3 | 25 | 20 |

As can be seen in Table 9 above, it could be seen that, in the antibacterial activity experiment performed in the presence of bovine serum, KU-5878 and KU-5878-K4 had lowered antibacterial activity, but the decrease in the antibacterial activity of KU-5878-K4-D was small compared to that of KU-5878-K4.

Example 5. Evaluation of Antibacterial Activity of Peptide in Which Some of Amino Acids Constituting KU-5878 are Modified In order to identify a peptide having better antibacterial activity and higher stability than KU-5878, the C-terminus of KU-5878 was amidated, and then the antibacterial activity of the peptide was comparatively evaluated using minimum bactericidal concentration assay. The experiment was performed in the same manner as in Example 1. Specific information on the KU-5878 variant and the MBC values thereof against each bacterium are shown in Table 10 below.

TABLE 10

| SEQ ID NO | Peptide | Amino acid sequence | MBC value (µg/ml) against Staphylococcus aureus | MBC value (µg/ml) against Pseudomonas aeruginosa |
|---|---|---|---|---|
| 13 | KU-5878-NH₂ (amidated) | KTMMQSGGTFGTFMAIGMGIR | 70 | 60 |

As shown in Table 10 above, it could be seen that the peptide obtained by modifying the terminus of KU-5878 had increased antibacterial activity.

Example 6. Evaluation of Antibacterial Activities of Peptides Obtained by Deletion of One Amino Acid from KU-5878

Variants were prepared by deleting one amino acid from the amino acid sequence of KU-5878 (SEQ ID NO: 13), and the antibacterial activities thereof were evaluated. The results of evaluation of the antibacterial activities are shown in Table 11 below.

As a result, when the amino acid sequence of KU-5878 is regarded to consist of the amino acids at positions 58 to 78, the deletion of the amino acid at position 60, 61, 62, 64, 65, 66, 68, 74, 75 or 76 led to an increase in the antibacterial activity. Considering that the same amino acids are contiguous, the deletion of M at position 61 is identical to the deletion of M at position 60, and the deletion of G at position 65 is identical to the deletion of G at position 64.

With respect to SEQ ID NO: 13, the deletion of the amino acid at position 3, 4, 5, 7, 8, 9, 11, 17, 18 or 19 led to an increase in the antibacterial activity.

Example 7. Evaluation of Antibacterial Activities of Peptides Obtained by Deletion of Two or More Amino Acids from KU-5878

Variants were prepared by deleting two or more amino acids from the amino acid sequence of KU-5878 (SEQ ID NO: 13), and the antibacterial activities thereof were evaluated. The results of evaluation of the antibacterial activities are shown in Table 12 below.

In most of the variants, except for the variant in which M at position 60 and G at position 64 were deleted, the antibacterial activity was lowered. Considering that the same amino acids are contiguous, the deletion of M at position 60 is identical to the deletion of M at position 61, and the deletion of G at position 64 is identical to the deletion of G at position 65.

With respect to SEQ ID NO: 13, the deletion of the amino acid at position 3 or 4 and the deletion of the amino acid at position 7 or 8 led to an increase in the antibacterial activity.

TABLE 11

| SEQ ID NO | Peptide name | Amino acid sequence | MBC Pseudomonas aeruginosa | Staphylococcus aureus | CRPA | MRSA | Increase in activity |
|---|---|---|---|---|---|---|---|
| 13 | 5878 | KTMMQSGGTFGTFMAIGMGIR | 100 | 100 | 110 | 100 | |
| 50 | 5878-d58K | -TMMQSGGTFGTFMAIGMGIR | 300 | 300 | 300 | >300 | |
| 51 | 5878-d59T | K-MMQSGGTFGTFMAIGMGIR | 150 | 150 | 150 | 150 | |
| 52 | 5878-d60M | KT-MQSGGTFGTFMAIGMGIR | 90 | 90 | 90 | 100 | o |
| 53 | 5878-d61M | KTM-QSGGTFGTFMAIGMGIR | 90 | 90 | 90 | 100 | o |
| 54 | 5878-d62Q | KTMM-SGGTFGTFMAIGMGIR | 100 | 90 | 100 | 100 | o |
| 55 | 5878-d63S | KTMMQ-GGTFGTFMAIGMGIR | 200 | 200 | 200 | 200 | |
| 56 | 5878-d64G | KTMMQS-GTFGTFMAIGMGIR | 100 | 100 | 110 | 100 | o |
| 57 | 5878-d65G | KTMMQSG-TFGTFMAIGMGIR | 100 | 100 | 110 | 100 | o |
| 58 | 5878-d66T | KTMMQSGG-FGTFMAIGMGIR | 90 | 90 | 100 | 90 | o |
| 59 | 5878-d67F | KTMMQSGGT-GTFMAIGMGIR | 200 | 200 | 200 | 200 | |
| 60 | 5878-d68G | KTMMQSGGTF-TFMAIGMGIR | 25 | 20 | 18 | 25 | o |
| 61 | 5878-d69T | KTMMQSGGTFG-FMAIGMGIR | 120 | 120 | 140 | 140 | |
| 62 | 5878-d70F | KTMMQSGGTFGT-MAIGMGIR | 200 | 200 | 200 | 200 | |
| 63 | 5878-d71M | KTMMQSGGTFGTF-AIGMGIR | 250 | 250 | 300 | 300 | |
| 64 | 5878-d72A | KTMMQSGGTFGTFM-IGMGIR | 150 | 150 | 170 | 160 | |
| 65 | 5878-d73I | KTMMQSGGTFGTFMA-GMGIR | >300 | >300 | >300 | >300 | |
| 66 | 5878-d74G | KTMMQSGGTFGTFMAI-MGIR | 20 | 25 | 30 | 25 | o |
| 67 | 5878-d75M | KTMMQSGGTFGTFMAIG-GIR | 100 | 100 | 100 | 110 | o |
| 68 | 5878-d76G | KTMMQSGGTFGTFMAIGM-IR | 80 | 70 | 90 | 90 | o |
| 69 | 5878-d77I | KTMMQSGGTFGTFMAIGMG-R | >300 | >300 | >300 | >300 | |
| 70 | 5878-d78R | KTMMQSGGTFGTFMAIGMGI- | 300 | 300 | >300 | >300 | |

TABLE 12

| SEQ ID NO | Peptide name | Amino acid sequence | MBC Pseudomonas aeruginosa | Staphylococcus aureus | CRPA | MRSA | increase in activity |
|---|---|---|---|---|---|---|---|
| 71 | 5878-d60M, d64G | KT-MQS-GTFGTFMAIGMGIR | 100 | 100 | 100 | 110 | O |
| 72 | 5878-d71M, d75M | KTMMQSGGTFGTF-AIG-GIR | 300 | 250 | 300 | 300 | |
| 73 | 5878-d60M, d72A, d75M | KT-MQSGGTFGTFM-IG-GIR | 300 | 280 | 300 | 300 | |
| 74 | 5878-d64G, d71M, d76G | KTMMQS-GTFGTF-AIGM-IR | 200 | 200 | 200 | 200 | |
| 75 | 5878-d60M, d64G, d72A, d75M | KT-MQS-GTFGTFM-IG-GIR | 120 | 100 | 120 | 120 | |
| 76 | 5878-d60M, d64G, d71M, d72A, d75M | KT-MQS-GTFGTF--IG-GIR | 200 | 200 | 200 | 200 | |

Example 8. Evaluation of Antibacterial Activities of Peptides Obtained by Substitution of One Amino Acid in KU-5878

One amino acid in the amino acid sequence of KU-5878 (SEQ ID NO: 13) was substituted, and the antibacterial activities of the peptides were evaluated. The results of evaluation of the antibacterial activities are shown in Table 13 below.

With respect to SEQ ID NO: 13, a K to R substitution at amino acid position 1, a T to K or R substitution at amino acid position 2, a Q to K or R substitution at amino acid position 5, an S to K, R or H substitution at amino acid position 6, a T to K or R substitution at amino acid position 9, an F to W substitution at amino acid position 10, an I to L substitution at amino acid position 16, or an I to G or L substitution at amino acid position 20 led to an increase in the antibacterial activity.

In addition, referring to KU-5878-4Nle in Table 13 below, it was confirmed that the antibacterial activity of the peptide was improved as a result of substituting all of four methionines in KU-5878 with norleucine. This is presumably because the structures of methionine and norleucine are identical to each other except that sulfur is changed to carbon.

TABLE 13

| SEQ ID NO | Peptide name | Amino acid sequence | MBC Pseudomonas aeruginosa | Staphylococcus aureus | CRPA | MRSA | Increase in activity |
|---|---|---|---|---|---|---|---|
| 13 | KU-5878 | KTMMQSGGTFGTFMAIGMGIR | 100 | 100 | 110 | 110 | |
| 77 | KU-5878-T59K | KKMMQSGGTFGTFMAIGMGIR | 50 | 40 | 50 | 50 | O |
| 78 | KU-5878-Q62K | KTMMKSGGTFGTFMAIGMGIR | 90 | 80 | 90 | 90 | O |
| 79 | KU-5878-S63K | KTMMQKGGTFGTFMAIGMGIR | 60 | 50 | 50 | 50 | O |
| 80 | KU-5878-T66K | KTMMQSGGKFGTFMAIGMGIR | 80 | 60 | 70 | 80 | O |
| 81 | KU-5878-T69K | KTMMQSGGTFGKFMAIGMGIR | 140 | 130 | 150 | 150 | |
| 82 | KU-5878-T59R | KRMMQSGGTFGTFMAIGMGIR | 30 | 25 | 30 | 30 | O |
| 83 | KU-5878-Q62R | KTMMRSGGTFGTFMAIGMGIR | 80 | 80 | 80 | 90 | O |
| 84 | KU-5878-S63R | KTMMQRGGTFGTFMAIGMGIR | 20 | 15 | 20 | 25 | O |
| 85 | KU-5878-T66R | KTMMQSGGRFGTFMAIGMGIR | 80 | 90 | 80 | 90 | O |
| 86 | KU-5878-T59H | KHMMQSGGTFGTFMAIGMGIR | >300 | >300 | >300 | >300 | |
| 87 | KU-5878-Q62H | KTMMHSGGTFGTFMAIGMGIR | >300 | >300 | >300 | >300 | |
| 88 | KU-5878-S63H | KTMMQHGGTFGTFMAIGMGIR | 100 | 100 | 100 | 110 | O |
| 89 | KU-5878-T66H | KTMMQSGGHFGTFMAIGMGIR | >300 | >300 | >300 | >300 | |
| 90 | KU-5878-T59S | KSMMQSGGTFGTFMAIGMGIR | >300 | >300 | >300 | >300 | |
| 91 | KU-5878-Q62S | KTMMSSGGTFGTFMAIGMGIR | >300 | >300 | >300 | >300 | |

TABLE 13-continued

| SEQ ID NO | Peptide name | Amino acid sequence | MBC Pseudomonas aeruginosa | MBC Staphylococcus aureus | CRPA | MRSA | Increase in activity |
|---|---|---|---|---|---|---|---|
| 92 | KU-5878-S63T | KTMMQTGGTFGTFMAIGMGIR | >300 | >300 | >300 | >300 | |
| 93 | KU-5878-T66S | KTMMQSGGSFGTFMAIGMGIR | >300 | >300 | >300 | >300 | |
| 94 | KU-5878-K58A | ATMMQSGGTFGTFMAIGMGIR | >300 | >300 | >300 | >300 | |
| 95 | KU-5878-T59A | KAMMQSGGTFGTFMAIGMGIR | 150 | 120 | 130 | 140 | |
| 96 | KU-5878-Q62A | KTMMASGGTFGTFMAIGMGIR | >300 | >300 | >300 | >300 | |
| 97 | KU-5878-S63A | KTMMQAGGTFGTFMAIGMGIR | 300 | 300 | 300 | >300 | |
| 98 | KU-5878-T66A | KTMMQSGGAFGTFMAIGMGIR | >300 | >300 | >300 | >300 | |
| 99 | KU-5878-T69A | KTMMQSGGTFGAFMAIGMGIR | 300 | 300 | 300 | 300 | |
| 100 | KU-5878-K58R | RTMMQSGGTFGTFMAIGMGIR | 120 | 120 | 120 | 120 | |
| 101 | KU-5878-K58A | ATMMQSGGTFGTFMAIGMGIR | >300 | >300 | >300 | >300 | |
| 102 | KU-5878-R78A | KTMMQSGGTFGTFMAIGMGIA | >300 | >300 | >300 | >300 | |
| 103 | KU-5878-R78K | KTMMQSGGTFGTFMAIGMGIK | >300 | >300 | >300 | >300 | |
| 104 | KU-5878-M60A | KTAMQSGGTFGTFMAIGMGIR | >300 | >300 | >300 | >300 | |
| 105 | KU-5878-I73A | KTMMQSGGTFGTFMAAGMGIR | >300 | >300 | >300 | >300 | |
| 106 | KU-5878-I73K | KTMMQSGGTFGTFMAKGMGIR | >300 | >300 | >300 | >300 | |
| 107 | KU-5878-I73W | KTMMQSGGTFGTFMAWGMGIR | 300 | 300 | 300 | >300 | |
| 108 | KU-5878-I77A | KTMMQSGGTFGTFMAIGMGAR | >300 | >300 | >300 | >300 | |
| 109 | KU-5878-I77K | KTMMQSGGTFGTFMAIGMGKR | >300 | >300 | >300 | >300 | |
| 110 | KU-5878-I77T | KTMMQSGGTFGTFMAIGMGTR | >300 | >300 | >300 | >300 | |
| 111 | KU-5878-I77G | KTMMQSGGTFGTFMAIGMGGR | 80 | 90 | 100 | 90 | O |
| 112 | KU-5878-4Nle | KT(Nle)(Nle)QSGGTFGTF(Nle)AIG(Nle)GIR | 110 | 90 | 100 | 100 | O |
| 113 | KU-5878-F67A | KTMMQSGGTAGTFMAIGMGIR | >300 | >300 | >300 | >300 | |
| 114 | KU-5878-F67W | KTMMQSGGTWGTFMAIGMGIR | 80 | 80 | 80 | 90 | O |
| 115 | KU-5878-F70K | KTMMQSGGTFGTKMAIGMGIR | >300 | >300 | >300 | >300 | |
| 116 | KU-5878-F70W | KTMMQSGGTFGTWMAIGMGIR | 300 | 300 | 300 | >300 | |
| 117 | KU-5878-A72G | KTMMQSGGTFGTFMGIGMGIR | >300 | >300 | >300 | >300 | |
| 118 | KU-5878-G76A | KTMMQSGGTFGTFMAIGMAIR | >300 | >300 | >300 | >300 | |

Example 9. Evaluation of Antibacterial Activities of Multi-Substituted Peptides Based on Substitution for Amino Acid at Position 59 in KU-5878

Substitutions of Q62K, S63K and T66K were sequentially added to the amino acid sequence of KU-5878-T59K, and the antibacterial activities of the peptides were evaluated. The results of evaluation of the antibacterial activity are shown in Table 14 below.

The substitution positions of T59K, Q62K, S63K and T66K correspond to the amino acids at positions 2, 5, 6, and 9 with respect to SEQ ID NO: 13.

TABLE 14

| SEQ ID NO | Peptide name | Amino acid sequence | MBC Pseudomonas aeruginosa | Staphylococcus aureus | CRPA | MRSA | Increase in activity |
|---|---|---|---|---|---|---|---|
| 13 | KU-5878 | KTMMQSGGTFGTFMAIGMGIR | 100 | 100 | 110 | 110 | |
| 119 | KU-5878-T59K | KKMMQSGGTFGTFMAIGMGIR | 50 | 40 | 50 | 50 | O |
| 120 | KU-5878-K2 (T59K, Q62K) | KKMMKSGGTFGTFMAIGMGIR | 8 | 8 | 6 | 8 | O |
| 121 | KU-5878-K3 (T59K, Q62K, S63K) | KKMMKKGGTFGTFMAIGMGIR | 4 | 4 | 4 | 5 | O |
| 122 | KU-5878-K4 (T59K, Q62K, S63K, T66K) | KKMMKKGGKFGTFMAIGMGIR | 4 | 3 | 3 | 4 | O |

Example 10. Evaluation of Antibacterial Activities of KU-5878 Comprising Amino Acid Sequence Added to C-Terminus An amino acid repeat sequence was added to the C-terminus of KU-5878, and the antibacterial activities of the peptides were evaluated. According to Table 15 below, when the R (arginine) repeat sequence or K (lysine) sequence was added to the C-terminus of KU-5878, the antibacterial activity of the peptide increased.

TABLE 15

| SEQ ID NO | Peptide name | Amino acid sequence | MBC Pseudomonas aeruginosa | Staphylococcus aureus | CRPA | MRSA | Increase in activity |
|---|---|---|---|---|---|---|---|
| 123 | 5878-3R | KTMMQSGGTFGTFMAIGMGIRRRR | 8 | 8 | 8 | 10 | O |
| 124 | 5878-KK | KTMMQSGGTFGTFMAIGMGIRKK | 15 | 16 | 16 | 16 | O |
| 125 | 5878-Q | KTMMQSGGTFGTFMAIGMGIRQ | 150 | 180 | 180 | 180 | |

Although the present invention has been described in detail with reference to the specific features, it will be apparent to those skilled in the art that this detailed description is only of a preferred embodiment thereof, and does not limit the scope of the present invention. Thus, the substantial scope of the present invention will be defined by the appended claims and equivalents thereto.

The invention claimed is:

1. A method for preventing or treating bacterial infectious disease comprising a step of administering a peptide consisting of the amino acid sequence of SEQ ID: 13 to a subject.

2. An antimicrobial agent comprising a peptide consisting of the amino acid sequence of any one of SEQ ID NOs: 17 to 23, 25, 27, 38, 39 and 42.

3. An antimicrobial agent comprising a peptide, the peptide consisting of an amino acid sequence SEQ ID NO: 13 having one amino acid substitution selected from among the following (b) to (h):
   (b) a T to K or R substitution at amino acid position 2,
   (c) a Q to K or R substitution at amino acid position 5,
   (d) an S to K, R or H substitution at amino acid position 6,
   (e) a T to K or R substitution at amino acid position 9,
   (f) an F to W substitution at amino acid position 10,
   (g) an I to L substitution at amino acid position 16, and
   (h) an I to G or L substitution at amino acid position 20.

4. An antimicrobial agent comprising a peptide, the peptide consisting of an amino acid sequence of SEQ IN NO: 13, having an amino acid sequence selected from RRR or KK linked to the C-terminus thereof.

* * * * *

SEQUENCE LISTING

<160> NUMBER OF SEQ ID NOS: 49

<210> SEQ ID NO 1
<211> LENGTH: 79
<212> TYPE: PRT
<213> ORGANISM: Artificial Sequence
<220> FEATURE:
<223> OTHER INFORMATION: Homo sapiens Romo1

<400> SEQUENCE: 1

Met Pro Val Ala Val Gly Pro Tyr Gly Gln Ser Gln Pro Ser Cys Phe
1               5                   10                  15

```
Asp Arg Val Lys Met Gly Phe Val Met Gly Cys Ala Val Gly Met Ala
            20                  25                  30

Ala Gly Ala Leu Phe Gly Thr Phe Ser Cys Leu Arg Ile Gly Met Arg
        35                  40                  45

Gly Arg Glu Leu Met Gly Gly Ile Gly Lys Thr Met Met Gln Ser Gly
    50                  55                  60

Gly Thr Phe Gly Thr Phe Met Ala Ile Gly Met Gly Ile Arg Cys
65                  70                  75

<210> SEQ ID NO 2
<211> LENGTH: 27
<212> TYPE: PRT
<213> ORGANISM: Artificial Sequence
<220> FEATURE:
<223> OTHER INFORMATION: KU-5278

<400> SEQUENCE: 2

Leu Met Gly Gly Ile Gly Lys Thr Met Met Gln Ser Gly Gly Thr Phe
1               5                   10                  15

Gly Thr Phe Met Ala Ile Gly Met Gly Ile Arg
            20                  25

<210> SEQ ID NO 3
<211> LENGTH: 28
<212> TYPE: PRT
<213> ORGANISM: Artificial Sequence
<220> FEATURE:
<223> OTHER INFORMATION: KU-5279

<400> SEQUENCE: 3

Leu Met Gly Gly Ile Gly Lys Thr Met Met Gln Ser Gly Gly Thr Phe
1               5                   10                  15

Gly Thr Phe Met Ala Ile Gly Met Gly Ile Arg Cys
            20                  25

<210> SEQ ID NO 4
<211> LENGTH: 25
<212> TYPE: PRT
<213> ORGANISM: Artificial Sequence
<220> FEATURE:
<223> OTHER INFORMATION: KU-5478

<400> SEQUENCE: 4

Gly Gly Ile Gly Lys Thr Met Met Gln Ser Gly Gly Thr Phe Gly Thr
1               5                   10                  15

Phe Met Ala Ile Gly Met Gly Ile Arg
            20                  25

<210> SEQ ID NO 5
<211> LENGTH: 26
<212> TYPE: PRT
<213> ORGANISM: Artificial Sequence
<220> FEATURE:
<223> OTHER INFORMATION: KU-5479

<400> SEQUENCE: 5

Gly Gly Ile Gly Lys Thr Met Met Gln Ser Gly Gly Thr Phe Gly Thr
1               5                   10                  15

Phe Met Ala Ile Gly Met Gly Ile Arg Cys
            20                  25

<210> SEQ ID NO 6
<211> LENGTH: 23
```

```
<212> TYPE: PRT
<213> ORGANISM: Artificial Sequence
<220> FEATURE:
<223> OTHER INFORMATION: KU-5678

<400> SEQUENCE: 6

Ile Gly Lys Thr Met Met Gln Ser Gly Gly Thr Phe Gly Thr Phe Met
1               5                   10                  15

Ala Ile Gly Met Gly Ile Arg
            20

<210> SEQ ID NO 7
<211> LENGTH: 24
<212> TYPE: PRT
<213> ORGANISM: Artificial Sequence
<220> FEATURE:
<223> OTHER INFORMATION: KU-5679

<400> SEQUENCE: 7

Ile Gly Lys Thr Met Met Gln Ser Gly Gly Thr Phe Gly Thr Phe Met
1               5                   10                  15

Ala Ile Gly Met Gly Ile Arg Cys
            20

<210> SEQ ID NO 8
<211> LENGTH: 22
<212> TYPE: PRT
<213> ORGANISM: Artificial Sequence
<220> FEATURE:
<223> OTHER INFORMATION: KU-5778

<400> SEQUENCE: 8

Gly Lys Thr Met Met Gln Ser Gly Gly Thr Phe Gly Thr Phe Met Ala
1               5                   10                  15

Ile Gly Met Gly Ile Arg
            20

<210> SEQ ID NO 9
<211> LENGTH: 23
<212> TYPE: PRT
<213> ORGANISM: Artificial Sequence
<220> FEATURE:
<223> OTHER INFORMATION: KU-5779

<400> SEQUENCE: 9

Gly Lys Thr Met Met Gln Ser Gly Gly Thr Phe Gly Thr Phe Met Ala
1               5                   10                  15

Ile Gly Met Gly Ile Arg Cys
            20

<210> SEQ ID NO 10
<211> LENGTH: 18
<212> TYPE: PRT
<213> ORGANISM: Artificial Sequence
<220> FEATURE:
<223> OTHER INFORMATION: KU-5875

<400> SEQUENCE: 10

Lys Thr Met Met Gln Ser Gly Gly Thr Phe Gly Thr Phe Met Ala Ile
1               5                   10                  15

Gly Met

<210> SEQ ID NO 11
<211> LENGTH: 19
```

```
<212> TYPE: PRT
<213> ORGANISM: Artificial Sequence
<220> FEATURE:
<223> OTHER INFORMATION: KU-5876

<400> SEQUENCE: 11

Lys Thr Met Met Gln Ser Gly Gly Thr Phe Gly Thr Phe Met Ala Ile
1               5                   10                  15

Gly Met Gly

<210> SEQ ID NO 12
<211> LENGTH: 20
<212> TYPE: PRT
<213> ORGANISM: Artificial Sequence
<220> FEATURE:
<223> OTHER INFORMATION: KU-5877

<400> SEQUENCE: 12

Lys Thr Met Met Gln Ser Gly Gly Thr Phe Gly Thr Phe Met Ala Ile
1               5                   10                  15

Gly Met Gly Ile
            20

<210> SEQ ID NO 13
<211> LENGTH: 21
<212> TYPE: PRT
<213> ORGANISM: Artificial Sequence
<220> FEATURE:
<223> OTHER INFORMATION: KU-5878

<400> SEQUENCE: 13

Lys Thr Met Met Gln Ser Gly Gly Thr Phe Gly Thr Phe Met Ala Ile
1               5                   10                  15

Gly Met Gly Ile Arg
            20

<210> SEQ ID NO 14
<211> LENGTH: 22
<212> TYPE: PRT
<213> ORGANISM: Artificial Sequence
<220> FEATURE:
<223> OTHER INFORMATION: KU-5879

<400> SEQUENCE: 14

Lys Thr Met Met Gln Ser Gly Gly Thr Phe Gly Thr Phe Met Ala Ile
1               5                   10                  15

Gly Met Gly Ile Arg Cys
            20

<210> SEQ ID NO 15
<211> LENGTH: 20
<212> TYPE: PRT
<213> ORGANISM: Artificial Sequence
<220> FEATURE:
<223> OTHER INFORMATION: KU-6079

<400> SEQUENCE: 15

Met Met Gln Ser Gly Gly Thr Phe Gly Thr Phe Met Ala Ile Gly Met
1               5                   10                  15

Gly Ile Arg Cys
            20

<210> SEQ ID NO 16
<211> LENGTH: 21
```

```
<212> TYPE: PRT
<213> ORGANISM: Artificial Sequence
<220> FEATURE:
<223> OTHER INFORMATION: Artificial peptide
<220> FEATURE:
<221> NAME/KEY: VARIANT
<222> LOCATION: (1)..(2)
<223> OTHER INFORMATION: X = any one of: R, K, H, S, T, Q, or N
<220> FEATURE:
<221> NAME/KEY: VARIANT
<222> LOCATION: (5)..(6)
<223> OTHER INFORMATION: X = any one of: R, K, H, S, T, Q, or N
<220> FEATURE:
<221> NAME/KEY: VARIANT
<222> LOCATION: (9)
<223> OTHER INFORMATION: X = any one of: R, K, H, S, T, Q, or N
<220> FEATURE:
<221> NAME/KEY: VARIANT
<222> LOCATION: (12)
<223> OTHER INFORMATION: X = any one of: R, K, H, S, T, Q, or N

<400> SEQUENCE: 16

Xaa Xaa Met Met Xaa Xaa Gly Gly Xaa Phe Gly Xaa Phe Met Ala Ile
1               5                   10                  15

Gly Met Gly Ile Arg
            20

<210> SEQ ID NO 17
<211> LENGTH: 21
<212> TYPE: PRT
<213> ORGANISM: Artificial Sequence
<220> FEATURE:
<223> OTHER INFORMATION: KU-5878-T59K

<400> SEQUENCE: 17

Lys Lys Met Met Gln Ser Gly Gly Thr Phe Gly Thr Phe Met Ala Ile
1               5                   10                  15

Gly Met Gly Ile Arg
            20

<210> SEQ ID NO 18
<211> LENGTH: 21
<212> TYPE: PRT
<213> ORGANISM: Artificial Sequence
<220> FEATURE:
<223> OTHER INFORMATION: KU-5878-Q62K

<400> SEQUENCE: 18

Lys Thr Met Met Lys Ser Gly Gly Thr Phe Gly Thr Phe Met Ala Ile
1               5                   10                  15

Gly Met Gly Ile Arg
            20

<210> SEQ ID NO 19
<211> LENGTH: 21
<212> TYPE: PRT
<213> ORGANISM: Artificial Sequence
<220> FEATURE:
<223> OTHER INFORMATION: KU-5878-S63K

<400> SEQUENCE: 19

Lys Thr Met Met Gln Lys Gly Gly Thr Phe Gly Thr Phe Met Ala Ile
1               5                   10                  15

Gly Met Gly Ile Arg
            20

<210> SEQ ID NO 20
```

```
<211> LENGTH: 21
<212> TYPE: PRT
<213> ORGANISM: Artificial Sequence
<220> FEATURE:
<223> OTHER INFORMATION: KU-5878-T66K

<400> SEQUENCE: 20

Lys Thr Met Met Gln Ser Gly Gly Lys Phe Gly Thr Phe Met Ala Ile
1               5                   10                  15

Gly Met Gly Ile Arg
            20

<210> SEQ ID NO 21
<211> LENGTH: 21
<212> TYPE: PRT
<213> ORGANISM: Artificial Sequence
<220> FEATURE:
<223> OTHER INFORMATION: KU-5878-T69K

<400> SEQUENCE: 21

Lys Thr Met Met Gln Ser Gly Gly Thr Phe Gly Lys Phe Met Ala Ile
1               5                   10                  15

Gly Met Gly Ile Arg
            20

<210> SEQ ID NO 22
<211> LENGTH: 21
<212> TYPE: PRT
<213> ORGANISM: Artificial Sequence
<220> FEATURE:
<223> OTHER INFORMATION: KU-5878-K2

<400> SEQUENCE: 22

Lys Lys Met Met Lys Ser Gly Gly Thr Phe Gly Thr Phe Met Ala Ile
1               5                   10                  15

Gly Met Gly Ile Arg
            20

<210> SEQ ID NO 23
<211> LENGTH: 21
<212> TYPE: PRT
<213> ORGANISM: Artificial Sequence
<220> FEATURE:
<223> OTHER INFORMATION: KU-5878-K3

<400> SEQUENCE: 23

Lys Lys Met Met Lys Lys Gly Gly Thr Phe Gly Thr Phe Met Ala Ile
1               5                   10                  15

Gly Met Gly Ile Arg
            20

<210> SEQ ID NO 24
<211> LENGTH: 21
<212> TYPE: PRT
<213> ORGANISM: Artificial Sequence
<220> FEATURE:
<223> OTHER INFORMATION: KU-5878-K4

<400> SEQUENCE: 24

Lys Lys Met Met Lys Lys Gly Gly Lys Phe Gly Thr Phe Met Ala Ile
1               5                   10                  15

Gly Met Gly Ile Arg
            20
```

```
<210> SEQ ID NO 25
<211> LENGTH: 21
<212> TYPE: PRT
<213> ORGANISM: Artificial Sequence
<220> FEATURE:
<223> OTHER INFORMATION: KU-5878-K58R

<400> SEQUENCE: 25

Arg Thr Met Met Gln Ser Gly Gly Thr Phe Gly Thr Phe Met Ala Ile
1               5                   10                  15

Gly Met Gly Ile Arg
            20

<210> SEQ ID NO 26
<211> LENGTH: 21
<212> TYPE: PRT
<213> ORGANISM: Artificial Sequence
<220> FEATURE:
<223> OTHER INFORMATION: KU-5878-K58A

<400> SEQUENCE: 26

Ala Thr Met Met Gln Ser Gly Gly Thr Phe Gly Thr Phe Met Ala Ile
1               5                   10                  15

Gly Met Gly Ile Arg
            20

<210> SEQ ID NO 27
<211> LENGTH: 21
<212> TYPE: PRT
<213> ORGANISM: Artificial Sequence
<220> FEATURE:
<223> OTHER INFORMATION: KU-5878-T59R

<400> SEQUENCE: 27

Lys Arg Met Met Gln Ser Gly Gly Thr Phe Gly Thr Phe Met Ala Ile
1               5                   10                  15

Gly Met Gly Ile Arg
            20

<210> SEQ ID NO 28
<211> LENGTH: 21
<212> TYPE: PRT
<213> ORGANISM: Artificial Sequence
<220> FEATURE:
<223> OTHER INFORMATION: KU-5878-R78A

<400> SEQUENCE: 28

Lys Thr Met Met Gln Ser Gly Gly Thr Phe Gly Thr Phe Met Ala Ile
1               5                   10                  15

Gly Met Gly Ile Ala
            20

<210> SEQ ID NO 29
<211> LENGTH: 21
<212> TYPE: PRT
<213> ORGANISM: Artificial Sequence
<220> FEATURE:
<223> OTHER INFORMATION: KU-5878-R78K

<400> SEQUENCE: 29

Lys Thr Met Met Gln Ser Gly Gly Thr Phe Gly Thr Phe Met Ala Ile
1               5                   10                  15

Gly Met Gly Ile Lys
            20
```

```
<210> SEQ ID NO 30
<211> LENGTH: 21
<212> TYPE: PRT
<213> ORGANISM: Artificial Sequence
<220> FEATURE:
<223> OTHER INFORMATION: artificial peptide
<220> FEATURE:
<221> NAME/KEY: VARIANT
<222> LOCATION: (3)..(4)
<223> OTHER INFORMATION: X = any one of: Met, Leu, Ile, Val, or Nle
<220> FEATURE:
<221> NAME/KEY: VARIANT
<222> LOCATION: (14)
<223> OTHER INFORMATION: X = any one of: Met, Leu, Ile, Val, or Nle
<220> FEATURE:
<221> NAME/KEY: VARIANT
<222> LOCATION: (16)
<223> OTHER INFORMATION: X = any one of: Met, Leu, Ile, Val, or Nle
<220> FEATURE:
<221> NAME/KEY: VARIANT
<222> LOCATION: (18)
<223> OTHER INFORMATION: X = any one of: Met, Leu, Ile, Val, or Nle
<220> FEATURE:
<221> NAME/KEY: VARIANT
<222> LOCATION: (20)
<223> OTHER INFORMATION: X = any one of: Met, Leu, Ile, Val, Gly, or Nle

<400> SEQUENCE: 30

Lys Thr Xaa Xaa Gln Ser Gly Gly Thr Phe Gly Thr Phe Xaa Ala Xaa
1               5                   10                  15

Gly Xaa Gly Xaa Arg
            20

<210> SEQ ID NO 31
<211> LENGTH: 21
<212> TYPE: PRT
<213> ORGANISM: Artificial Sequence
<220> FEATURE:
<223> OTHER INFORMATION: KU-5878-M60A

<400> SEQUENCE: 31

Lys Thr Ala Met Gln Ser Gly Gly Thr Phe Gly Thr Phe Met Ala Ile
1               5                   10                  15

Gly Met Gly Ile Arg
            20

<210> SEQ ID NO 32
<211> LENGTH: 21
<212> TYPE: PRT
<213> ORGANISM: Artificial Sequence
<220> FEATURE:
<223> OTHER INFORMATION: KU-5878-I73A

<400> SEQUENCE: 32

Lys Thr Met Met Gln Ser Gly Gly Thr Phe Gly Thr Phe Met Ala Ala
1               5                   10                  15

Gly Met Gly Ile Arg
            20

<210> SEQ ID NO 33
<211> LENGTH: 21
<212> TYPE: PRT
<213> ORGANISM: Artificial Sequence
<220> FEATURE:
<223> OTHER INFORMATION: KU-5878-I73K

<400> SEQUENCE: 33

Lys Thr Met Met Gln Ser Gly Gly Thr Phe Gly Thr Phe Met Ala Lys
```

Gly Met Gly Ile Arg
            20

<210> SEQ ID NO 34
<211> LENGTH: 21
<212> TYPE: PRT
<213> ORGANISM: Artificial Sequence
<220> FEATURE:
<223> OTHER INFORMATION: KU-5878-I73W

<400> SEQUENCE: 34

Lys Thr Met Met Gln Ser Gly Gly Thr Phe Gly Thr Phe Met Ala Trp
1               5                   10                  15

Gly Met Gly Ile Arg
            20

<210> SEQ ID NO 35
<211> LENGTH: 21
<212> TYPE: PRT
<213> ORGANISM: Artificial Sequence
<220> FEATURE:
<223> OTHER INFORMATION: KU-5878-I77A

<400> SEQUENCE: 35

Lys Thr Met Met Gln Ser Gly Gly Thr Phe Gly Thr Phe Met Ala Ile
1               5                   10                  15

Gly Met Gly Ala Arg
            20

<210> SEQ ID NO 36
<211> LENGTH: 21
<212> TYPE: PRT
<213> ORGANISM: Artificial Sequence
<220> FEATURE:
<223> OTHER INFORMATION: KU-5878-I77K

<400> SEQUENCE: 36

Lys Thr Met Met Gln Ser Gly Gly Thr Phe Gly Thr Phe Met Ala Ile
1               5                   10                  15

Gly Met Gly Lys Arg
            20

<210> SEQ ID NO 37
<211> LENGTH: 21
<212> TYPE: PRT
<213> ORGANISM: Artificial Sequence
<220> FEATURE:
<223> OTHER INFORMATION: KU-5878-I77T

<400> SEQUENCE: 37

Lys Thr Met Met Gln Ser Gly Gly Thr Phe Gly Thr Phe Met Ala Ile
1               5                   10                  15

Gly Met Gly Thr Arg
            20

<210> SEQ ID NO 38
<211> LENGTH: 21
<212> TYPE: PRT
<213> ORGANISM: Artificial Sequence
<220> FEATURE:
<223> OTHER INFORMATION: KU-5878-I77G

<400> SEQUENCE: 38

-continued

```
Lys Thr Met Met Gln Ser Gly Gly Thr Phe Gly Thr Phe Met Ala Ile
1               5                   10                  15

Gly Met Gly Gly Arg
            20

<210> SEQ ID NO 39
<211> LENGTH: 21
<212> TYPE: PRT
<213> ORGANISM: Artificial Sequence
<220> FEATURE:
<223> OTHER INFORMATION: KU-5878-4Nle
<220> FEATURE:
<221> NAME/KEY: VARIANT
<222> LOCATION: (3)..(4)
<223> OTHER INFORMATION: X = Norleucine(Nle)
<220> FEATURE:
<221> NAME/KEY: VARIANT
<222> LOCATION: (14)
<223> OTHER INFORMATION: X = Norleucine(Nle)
<220> FEATURE:
<221> NAME/KEY: VARIANT
<222> LOCATION: (18)
<223> OTHER INFORMATION: X = Norleucine(Nle)

<400> SEQUENCE: 39

Lys Thr Xaa Xaa Gln Ser Gly Gly Thr Phe Gly Thr Phe Xaa Ala Ile
1               5                   10                  15

Gly Xaa Gly Ile Arg
            20

<210> SEQ ID NO 40
<211> LENGTH: 21
<212> TYPE: PRT
<213> ORGANISM: Artificial Sequence
<220> FEATURE:
<223> OTHER INFORMATION: Artificial peptide
<220> FEATURE:
<221> NAME/KEY: VARIANT
<222> LOCATION: (10)
<223> OTHER INFORMATION: X = any one of: F, Y, or W
<220> FEATURE:
<221> NAME/KEY: VARIANT
<222> LOCATION: (13)
<223> OTHER INFORMATION: X = any one of: F, Y, or W

<400> SEQUENCE: 40

Lys Thr Met Met Gln Ser Gly Gly Thr Xaa Gly Thr Xaa Met Ala Ile
1               5                   10                  15

Gly Met Gly Ile Arg
            20

<210> SEQ ID NO 41
<211> LENGTH: 21
<212> TYPE: PRT
<213> ORGANISM: Artificial Sequence
<220> FEATURE:
<223> OTHER INFORMATION: KU-5878-F67A

<400> SEQUENCE: 41

Lys Thr Met Met Gln Ser Gly Gly Thr Ala Gly Thr Phe Met Ala Ile
1               5                   10                  15

Gly Met Gly Ile Arg
            20

<210> SEQ ID NO 42
<211> LENGTH: 21
<212> TYPE: PRT
<213> ORGANISM: Artificial Sequence
```

```
<220> FEATURE:
<223> OTHER INFORMATION: KU-5878-F67W

<400> SEQUENCE: 42

Lys Thr Met Met Gln Ser Gly Gly Thr Trp Gly Thr Phe Met Ala Ile
1               5                   10                  15

Gly Met Gly Ile Arg
            20

<210> SEQ ID NO 43
<211> LENGTH: 21
<212> TYPE: PRT
<213> ORGANISM: Artificial Sequence
<220> FEATURE:
<223> OTHER INFORMATION: KU-5878-F70K

<400> SEQUENCE: 43

Lys Thr Met Met Gln Ser Gly Gly Thr Phe Gly Thr Lys Met Ala Ile
1               5                   10                  15

Gly Met Gly Ile Arg
            20

<210> SEQ ID NO 44
<211> LENGTH: 21
<212> TYPE: PRT
<213> ORGANISM: Artificial Sequence
<220> FEATURE:
<223> OTHER INFORMATION: KU-5878-F70W

<400> SEQUENCE: 44

Lys Thr Met Met Gln Ser Gly Gly Thr Phe Gly Thr Trp Met Ala Ile
1               5                   10                  15

Gly Met Gly Ile Arg
            20

<210> SEQ ID NO 45
<211> LENGTH: 21
<212> TYPE: PRT
<213> ORGANISM: Artificial Sequence
<220> FEATURE:
<223> OTHER INFORMATION: artificial peptide
<220> FEATURE:
<221> NAME/KEY: VARIANT
<222> LOCATION: (7)..(8)
<223> OTHER INFORMATION: X = any one of: A or G
<220> FEATURE:
<221> NAME/KEY: VARIANT
<222> LOCATION: (11)
<223> OTHER INFORMATION: X = any one of: A or G
<220> FEATURE:
<221> NAME/KEY: VARIANT
<222> LOCATION: (15)
<223> OTHER INFORMATION: X = any one of: A or G
<220> FEATURE:
<221> NAME/KEY: VARIANT
<222> LOCATION: (17)
<223> OTHER INFORMATION: X = any one of: A or G
<220> FEATURE:
<221> NAME/KEY: VARIANT
<222> LOCATION: (19)
<223> OTHER INFORMATION: X = any one of: A or G

<400> SEQUENCE: 45

Lys Thr Met Met Gln Ser Xaa Xaa Thr Phe Xaa Thr Phe Met Xaa Ile
1               5                   10                  15

Xaa Met Xaa Ile Arg
            20
```

```
<210> SEQ ID NO 46
<211> LENGTH: 21
<212> TYPE: PRT
<213> ORGANISM: Artificial Sequence
<220> FEATURE:
<223> OTHER INFORMATION: KU-5878-A72G

<400> SEQUENCE: 46

Lys Thr Met Met Gln Ser Gly Gly Thr Phe Gly Thr Phe Met Gly Ile
1               5                   10                  15

Gly Met Gly Ile Arg
            20

<210> SEQ ID NO 47
<211> LENGTH: 21
<212> TYPE: PRT
<213> ORGANISM: Artificial Sequence
<220> FEATURE:
<223> OTHER INFORMATION: KU-5878-G76A

<400> SEQUENCE: 47

Lys Thr Met Met Gln Ser Gly Gly Thr Phe Gly Thr Phe Met Ala Ile
1               5                   10                  15

Gly Met Ala Ile Arg
            20

<210> SEQ ID NO 48
<211> LENGTH: 19
<212> TYPE: PRT
<213> ORGANISM: Artificial Sequence
<220> FEATURE:
<223> OTHER INFORMATION: pCM19

<400> SEQUENCE: 48

Cys Leu Arg Ile Gly Met Arg Gly Arg Glu Leu Met Gly Gly Ile Gly
1               5                   10                  15

Lys Thr Met

<210> SEQ ID NO 49
<211> LENGTH: 18
<212> TYPE: PRT
<213> ORGANISM: Artificial Sequence
<220> FEATURE:
<223> OTHER INFORMATION: pCM12

<400> SEQUENCE: 49

Lys Thr Met Met Gln Ser Gly Gly Thr Phe Gly Thr Phe Met Met Gly
1               5                   10                  15

Ile Arg
```